US006773914B1

(12) United States Patent
Handler

(10) Patent No.: US 6,773,914 B1
(45) Date of Patent: Aug. 10, 2004

(54) PIGGYBAC TRANSFORMATION SYSTEM

(75) Inventor: Alfred M. Handler, Gainesville, FL (US)

(73) Assignee: The United States of America as represented by the Secretary of Agriculture, Washington, DC (US)

(*) Notice: Subject to any disclaimer, the term of this patent is extended or adjusted under 35 U.S.C. 154(b) by 0 days.

(21) Appl. No.: 09/377,066

(22) Filed: Aug. 19, 1999

(51) Int. Cl.[7] .................. C12N 15/00; C07H 21/02; C07H 21/04

(52) U.S. Cl. .................. 435/320.1; 536/23.1; 536/23.5

(58) Field of Search .................. 435/320.1, 455; 800/13, 14, 19, 20

(56) References Cited

PUBLICATIONS

O'Brochta et al., "Transposable Elements and Gene Transformation in Non–Drosophilid Insects", *Insect Biochemistry Molecular Biology*, vol. 26(8–9), pp. 739–753, 1996.
Lis et al., "New Heat Shock Puffs and β–Galactosidase Activity Resulting from Transformation of Drosophila with an hsp70–LacZ Hybrid Gene", *Cell*, vol. 35, pp. 403–410, 1983( Part 1).
Lohe et al., "Germline Transformation of *Drosophila virilis* with the Transposable Element mariner", *Genetics*, vol. 143, pp. 365–374, 1996.
Loukeris et al., "Gene Transfer into the Medfly, *Ceratitis capitata* with a *Drosophila hydei* Transposable Element", *Science*, vol. 270, pp. 2002–2005, 1995.
Lozovskaya et al., "Germline Transformation of *Drosophila virilis* Mediated by the Transposable Element hobo", *Genetics*, vol. 142, pp. 173–177, 1996.
O'Brochta et al., "Hermes, a Functional Non–Drosophilid Insect Gene Vector From *Musca domestica*", *Genetics*, vol. 142, pp. 907–914, 1996.
Pirrotta et al., "Muliple upstream regulatory elements control the expression of the Drosophila white gene", *EMBO Journal*, vol. 4(13A), pp. 3501–3508, 1985.
Ashburner et al., "Prospects for the genetic transformation of arthropods", *Insect Molecular Biology*, vol. 7(3), pp. 201–213, 1998.
Bhadra et al., "Interactions Among Dosage–Dependent Trans–Acting Modifiers of Gene Expression and Position–Effect Variegation in Drosophila", *Genetics*, vol. 150, pp. 251–263, 1998.
Coates et al., "Mariner transposition and transformation of the yellow fever mosquito, *Aedes aegypti*", *Genetics*, vol. 95, pp. 3748–3751, 1998.
Chalfie et al., "Green Fluorescent Protein as a Marker for Gene Expression", *Science*, vol. 63, pp. 802–805, 1994.
Cormack et al., "ACS–optimized mutants of the green fluorescent protein (GFP)", *Science*, vol. 173, pp. 33–38, 1996.

Davis et al., "A Nuclear GFP that Marks Nuclei in Living Drosophila Embryos; Maternal Supply Overcomes a Delay in the Appearance of Zygotic Fluorescence", *Developmental Biology*, vol. 170, pp. 726–729, 1995.
Elick et al., "PCR analysis of insertion site specificity, transcription, and structural uniformity of the Lepidopteran transposable element IFP2 in the TN–368 cell genome", *Genetica*, vol. 97, pp. 127–139, 1996.
Franz et al., "Mobile Minos elements from *Drosophila hydei* encode a two–exon transposase with similarity to the paired DNA–binding domain", *Proc. Natl. Acad. Science*, vol. 91, pp. 4746–4750, 1994.
Gomez et al., "A *Drosophila melanogaster* hobo–white+ vector mediates low frequency gene transfer in D. virilis with full interspecific white[+] complementation", *Insect Molecular Biology*, vol. 6(2), pp. 165–171, 1997.
Hazelrigg et al., "Transformation of white Locus DNA in Drosophila: Dosage Compensation, zeste Interaction, and Position Effects", *Cell*, vol. 36, pp. 469–481, 1984.
Jacobson et al., "Molecular structure of a somatically unstable transposable element in Drosophila", *Proc. Natl. Acad. Science*, vol. 83, pp. 8684–8688, 1986.
Jasinskiene et al., "Stable transformation of the yellow fever mosquito, *Aedes aegypti*, with the Hermes element from the housefly", *Genetics*, pp. 3743–3747, 1998.
Lanford et al., "Induction of Nuclear Transport with a Synthetic Peptide Homologous to the SV40 Antigen Transport Signal", *Cell*, vol. 46, pp. 575–582, 1986.
Lee et al., "Structure and Expression of Ubiquitin Genes of *Drosophila melanogaster*", *Molecular and Cellular Biology*, vol. 8 (11), pp. 4727–4735, 1988.
Lidholm et al., "The Transposable Element mariner Mediates Germline Transformation in *Drosophila melanogaster*", *Genetics*, vol. 134, pp. 859–868, 1993.
Franz et al., "Minos, a new transposable element from *Drosophila hydei*, is a member of the Tc1–like family of transposons", *Nucleic Acids Research*, vol. 19 (23), p. 646, 1991.
Prasher et al., "Primary structure of the *Aequorea victoria* green–fluorescent protein", *Gene*, vol. 111, pp. 229–233, 1992.

(List continued on next page.)

*Primary Examiner*—Scott D. Priebe
*Assistant Examiner*—Shin-Lin Chen
(74) *Attorney, Agent, or Firm*—M. Howard Silverstein; John D. Fado; Gail E. Poulos

(57) ABSTRACT

The present invention is directed to a transformation system for making transgenic organisms that includes a vector containing a modified piggyBac transposon into which is inserted an enhanced green fluorescent protein gene linked to a polyubiquitin promoter sequence and a nuclear localizing sequence; and a helper transposase vector that includes an hsp70 promoter sequence upstream of the putative piggyBac promoter that increases the transformation frequency of this system.

1 Claim, 19 Drawing Sheets

(5 of 19 Drawing Sheet(s) Filed in Color)

OTHER PUBLICATIONS

Rubin et al., "Genetic Transformation of Drosophila with Transposable Element Vectors", *Science,* vol. 218, pp. 348–353, 1982.

Smith et al., "hobo Enhancer Trapping Mutagenesis in Drosphila Reveals an Insertion Specificity Different from P Elements", *Genetics,* vol. 135, pp. 1063–1076, 1993.

Wang et al., "Implications for bcd mRNA localization from spatial distribution of exu protein in *Drosophila oogenesis*", *Nature,* vol. 369, pp. 400–403, 1994.

Warren et al., "The Hermes transposable element from the house fly, *Musca domestica,* is a short inverted repeat–type element of the hobo, Ac, and Tam3 (hAT) element family", pp. 87–97, 1994.

Ahmed et al., "Use of ordered deletions in genome sequencing", *Gene,* vol. 197, pp. 367–373, 1997.

Cary et al., "Transposon Mutagenesis of Baculoviruses: Analysis of Trichoplusia ni Transposon IFP2 Insertions within the FP–Locus of Nuclear Polyhedrosis Viruses", *Virology,* vol. 172, pp. 156–169, 1989.

Yang et al., "Optimized codon usage and chromophore mutations provide enhanced sensitivity with the green fluorescent protein", *Nucleic Acids Research,* vol. 24 (22), pp. 4592–4593, 1996.

Handler et al., "The lepidopteran transposon vector, piggy-Bac, mediates germ–line transformation in the Mediterranean fruit fly", *Proc. Natl. Acad. Science USA,* vol. 95, pp. 7520–7525, 1998.

| | | |
|---|---|---|
| p3E1.2 | aagccgcaaatctttTTAA-*piggyBac*-TTAAataatagtttctaat | |
| F1-2 | aaaagactgactatTTAA-*piggyBac*-TTAAtaagcacactgagtc | |
| M17-4 | aaatgtcgtctaggTTAA-*piggyBac*-TTAAagccgtatatcagat | |
| M31-6 | aaatgaacgactttTTAA-*piggyBac*-TTAAtggttttttagttgt | |

FIG. 4b

```
              10         20         30         40         50
          1234567890 1234567890 1234567890 1234567890 1234567890
          GACGAAAGGG CCTCGTGATA CGCCTATTTT TATAGGTTAA TGTCATGATA     50
          ATAATGGTTT CTTAGACGTC AGGTGGCACT TTTCGGGGAA ATGTGCGCGG    100
          AACCCCTATT TGTTTATTTT TCTAAATACA TTCAAATATG TATCCGCTCA    150
          TGAGACAATA ACCCTGATAA ATGCTTCAAT AATATTGAAA AAGGAAGAGT    200
          ATGAGTATTC AACATTTCCG TGTCGCCCTT ATTCCCTTTT TTGCGGCATT    250
          TTGCCTTCCT GTTTTTGCTC ACCCAGAAAC GCTGGTGAAA GTAAAAGATG    300
          CTGAAGATCA GTTGGGTGCA CGAGTGGGTT ACATCGAACT GGATCTCAAC    350
          AGCGGTAAGA TCCTTGAGAG TTTTCGCCCC GAAGAACGTT TTCCAATGAT    400
          GAGCACTTTT AAAGTTCTGC TATGTGGCGC GGTATTATCC CGTATTGACG    450
          CCGGGCAAGA GCAACTCGGT CGCCGCATAC ACTATTCTCA GAATGACTTG    500
          GTTGAGTACT CACCAGTCAC AGAAAAGCAT CTTACGGATG GCATGACAGT    550
          AAGAGAATTA TGCAGTGCTG CCATAACCAT GAGTGATAAC ACTGCGGCCA    600
          ACTTACTTCT GACAACGATC GGAGGACCGA AGGAGCTAAC CGCTTTTTTG    650
          CACAACATGG GGGATCATGT AACTCGCCTT GATCGTTGGG AACCGGAGCT    700
          GAATGAAGCC ATACCAAACG ACGAGCGTGA CACCACGATG CCTGTAGCAA    750
          TGGCAACAAC GTTGCGCAAA CTATTAACTG GCGAACTACT TACTCTAGCT    800
          TCCCGGCAAC AATTAATAGA CTGGATGGAG GCGGATAAAG TTGCAGGACC    850
          ACTTCTGCGC TCGGCCCTTC CGGCTGGCTG GTTTATTGCT GATAAATCTG    900
          GAGCCGGTGA GCGTGGGTCT CGCGGTATCA TTGCAGCACT GGGGCCAGAT    950
          GGTAAGCCCT CCCGTATCGT AGTTATCTAC ACGACGGGGA GTCAGGCAAC   1000
          TATGGATGAA CGAAATAGAC AGATCGCTGA GATAGGTGCC TCACTGATTA   1050
          AGCATTGGTA ACTGTCAGAC CAAGTTTACT CATATATACT TTAGATTGAT   1100
          TTAAAACTTC ATTTTTAATT TAAAAGGATC TAGGTGAAGA TCCTTTTTGA   1150
          TAATCTCATG ACCAAAATCC CTTAACGTGA GTTTTCGTTC CACTGAGCGT   1200
          CAGACCCCGT AGAAAAGATC AAAGGATCTT CTTGAGATCC TTTTTTTCTG   1250
          CGCGTAATCT GCTGCTTGCA AACAAAAAAA CCACCGCTAC CAGCGGTGGT   1300
          TTGTTTGCCG GATCAAGAGC TACCAACTCT TTTTCCGAAG GTAACTGGCT   1350
          TCAGCAGAGC GCAGATACCA AATACTGTCC TTCTAGTGTA GCCGTAGTTA   1400
          GGCCACCACT TCAAGAACTC TGTAGCACCG CCTACATACC TCGCTCTGCT   1450
          AATCCTGTTA CCAGTGGCTG CTGCCAGTGG CGATAAGTCG TGTCTTACCG   1500
          GGTTGGACTC AAGACGATAG TTACCGGATA AGGCGCAGCG GTCGGGCTGA   1550
          ACGGGGGGTT CGTGCACACA GCCCAGCTTG GAGCGAACGA CCTACACCGA   1600
          ACTGAGATAC CTACAGCGTG AGCATTGAGA AAGCGCCACG CTTCCCGAAG   1650
          GGAGAAAGGC GGACAGGTAT CCGGTAAGCG GCAGGGTCGG AACAGGAGAG   1700
          CGCACGAGGG AGCTTCCAGG GGGAAACGCC TGGTATCTTT ATAGTCCTGT   1750
          CGGGTTTCGC CACCTCTGAC TTGAGCGTCG ATTTTTGTGA TGCTCGTCAG   1800
```

FIG. 6a

|  | 10 | 20 | 30 | 40 | 50 |  |
|---|---|---|---|---|---|---|
|  | 1234567890 | 1234567890 | 1234567890 | 1234567890 | 1234567890 |  |
|  | GGGGGCGGAG | CCTATGGAAA | AACGCCAGCA | ACGCGGCCTT | TTTACGGTTC | 1850 |
|  | CTGGCCTTTT | GCTGGCCTTT | TGCTCACATG | TTCTTTCCTG | CGTTATCCCC | 1900 |
|  | TGATTCTGTG | GATAACCGTA | TTACCGCCTT | TGAGTGAGCT | GATACCGCTC | 1950 |
|  | GCCGCAGCCG | AACGACCGAG | CGCAGCGAGT | CAGTGAGCGA | GGAAGCGGAA | 2000 |
|  | GAGCGCCCAA | TACGCAAACC | GCCTCTCCCC | GCGCGTTGGC | CGATTCATTA | 2050 |
|  | ATGCAGCTGG | CACGACAGGT | TTCCCGACTG | GAAAGCGGGC | AGTGAGCGCA | 2100 |
|  | ACGCAATTAA | TGTGAGTTAG | CTCACTCATT | AGGCACCCCA | GGCTTTACAC | 2150 |
|  | TTTATGCTTC | CGGCTCGTAT | GTTGTGTGGA | ATTGTGAGCG | GATAACAATT | 2200 |
|  | TCACACAGGA | AACAGCTATG | ACCATGATTA | CGAATTCGAG | CTCGGTACCC | 2250 |
|  | GGGGATCCTC | TAGAGTCGAC | CTGCAGGCAT | GCAAGCTTGC | ATGCCTGCAG | 2300 |
|  | GTCGACGCTC | GCGCGACTTG | GTTTGCCATT | CTTTAGCGCG | CGTCGCGTCA | 2350 |
|  | CACAGCTTGG | CCACAATGTG | GTTTTTGTCA | AACGAAGATT | CTATGACGTG | 2400 |
|  | TTTAAAGTTT | AGGTCGAGTA | AAGCGCAAAT | CTTTTTAAC | CCTAGAAAGA | 2450 |
|  | TAGTCTGCGT | AAAATTGACG | CATGCATTCT | TGAAATATTG | CTCTCTCTTT | 2500 |
|  | CTAAATAGCG | CGAATCCGTC | GCTGTGCATT | TAGGACATCT | CAGTCGCCGC | 2550 |
|  | TTGGAGCTCC | CGTGAGGCGT | GCTTGTCAAT | GCGGTAAGTG | TCACTGATTT | 2600 |
|  | TGAACTATAA | CGACCGCGTG | AGTCAAAATG | ACGCATGATT | ATCTTTTACG | 2650 |
|  | TGACTTTTAA | GATTTAACTC | ATACGATAAT | TATATTGTTA | TTTCATGTTC | 2700 |
|  | TACTTACGTG | ATAACTTATT | ATATATATAT | TTTCTTGTTA | TAGATATCGT | 2750 |
|  | GACTAATATA | TAATAAAATG | GGTAGTTCTT | TAGACGATGA | GCATATCCTC | 2800 |
|  | TCTGCTCTTC | TGCAAAGCGA | TGACGAGCTT | GTTGGTGAGG | ATTCTGACAG | 2850 |
|  | TGAAATATCA | GATCACGTAA | GTGAAGATGA | CGTCCAGAGC | GATACAGAAG | 2900 |
|  | AAGCGTTTAT | AGATGAGGTA | CATGAAGTGC | AGCCAACGTC | AAGCGGTAGT | 2950 |
|  | GAAATATTAG | ACGAACAAAA | TGTTATTGAA | CAACCAGGTT | CTTCATTGGC | 3000 |
|  | TTCTAACAGA | ATCTTGACCT | TGCCACAGAG | GACTATTAGA | GGTAAGAATA | 3050 |
|  | AACATTGTTG | GTCAACTTCA | AAGTCCACGA | GGCGTAGCCG | AGTCTCTGCA | 3100 |
|  | CTGAACATTG | TCAGATCTCG | AGCTCAAGCT | TCGAATTCTG | CAGTCGACGG | 3150 |
|  | TACCCGATCT | TGTCGCCGGA | ACGCAGCGAC | AGAGATTCCA | ATGTGTCCGT | 3200 |
|  | ATCTTTCAGG | CTTTTGCCCT | TCAGTTCCAG | ACGAAGCGAC | TGGCGATTCG | 3250 |
|  | CGTGTGGGT | CTGCTTCAGG | GTCTTGTGAA | TTAGGGCGCC | CAGATCGCCG | 3300 |
|  | ATGGGCGTGG | CGCCGGAGGG | CACCTTCACC | TTGCCGTACG | GCTTGCTGTT | 3350 |
|  | CTTCGCGTTC | AAAATCTCCA | GCTCCATTTT | GCTTTCGGTG | CGCTTGCAAT | 3400 |
|  | CAGTACTGTC | CAAAATCGAA | AATCGCCGAA | CCGTAGTGTG | ACCGTGCGGG | 3450 |
|  | GCTCTGCGAA | AATAAACTTT | TTTAGGTATA | TGGCCACACA | CGGGGAAAGC | 3500 |
|  | ACAGTGGATT | ATATGTTTTA | ATATTATAAT | ATGCAGGTTT | TCATTACTTA | 3550 |
|  | TCCAGATGTA | AGCCCACTTA | AAGCGATTTA | ACAATTATTT | GCCGAAAGAG | 3600 |

Fig. 6b

|  | 10 | 20 | 30 | 40 | 50 |  |
|---|---|---|---|---|---|---|
|  | 1234567890 | 1234567890 | 1234567890 | 1234567890 | 1234567890 |  |
|  | TAAAAACAAA | TTTCACTTAA | AAATGGATTA | AGAAAAGCTT | GTGTAAGATT | 3650 |
|  | ATGCGCAGCG | TTGCCAGATA | GCTCCATTTA | AAACACTTCA | AAACAATAA | 3700 |
|  | GTTTTGAAAA | TATATACATA | AATAGCAGTC | GTTGCCGCAA | CGCTCAACAC | 3750 |
|  | ATCACACTTT | TAAAACACCC | TTTACCTACA | CAGAATTACT | TTTTAAATTT | 3800 |
|  | CCAGTCAAGC | TGCGAGTTTC | AAAATTATAG | CCGGTAGAGA | AGACAGTGCT | 3850 |
|  | ATTTCAAAAG | CAAACTAAAT | AAACACCAAT | CCTAACAAGC | CTTGGACTTT | 3900 |
|  | TGTAAGTTTA | GATCAAAGGT | GGCATTGCAT | TCAATGTCAT | GGTAAGAAGT | 3950 |
|  | AGGTCGTCTA | GGTAGAAATC | CTCATTCAGC | CGGTCAAGTC | AGTACGAGAA | 4000 |
|  | AGGTCTCAAT | TTGAAATTGT | CTTAAAAATA | TTTTATTGTT | TTGTACTGTG | 4050 |
|  | GTGAGTTTAA | ACGAAAAACA | CAAAAAAAAA | GTGATACACA | GAAATCATAA | 4100 |
|  | AAAATTTTAA | TACAAGGTAT | TGTACGTAT | CAAAAACATT | TCGGCACAAT | 4150 |
|  | TTTTTTCTC | TGTACTAAAG | TGTTACGAAC | ACTACGGTAT | TTTTTAGTGA | 4200 |
|  | TTTTCAACGG | ACACCGAAGG | TATATAAACA | GCGTTCGCGA | ACGGTCGCCT | 4250 |
|  | TCAAAACCAA | TTGACATTTG | CAGCAGCAAG | TACAAGCAGA | AAGTAAAGCG | 4300 |
|  | CAATCAGCGA | AAAATTTATA | CTTAATTGTT | GGTGATTAAA | GTACAATTAA | 4350 |
|  | AAGAACATTC | TCGAAAGTCA | CAAGAAACGT | AAGTTTTTAA | CTCGCTGTTA | 4400 |
|  | CCAATTAGTA | ATAAGAGCAA | CAAGACGTTG | AGTAATTTCA | AGAAAAACTG | 4450 |
|  | CATTTCAAGG | TCTTTGTTCG | GCCATTTTTT | TTTTATTCAA | CGCTCTACGT | 4500 |
|  | AATTACAAAA | TAAGAAATTG | GCAGCCACGC | ATCTTGTTTT | CCCAATCAAT | 4550 |
|  | TGGCATCAAA | ACGCAAACAA | ATCTATAAAT | AAAACTTGCG | TGTTGATTTT | 4600 |
|  | CGCCAAGATT | TATTGGCAAA | TTGTGAAATT | CGCAGTGACG | CATTTGAAAA | 4650 |
|  | TTCGAGAAAT | CACGAACGCA | CTCGAGCATT | TGTGTGCATG | TTATTAGTTA | 4700 |
|  | GTTAGTTCTT | TGCTTAATTG | AAGTATTTTA | CCAACGAAAT | CCACTTATTT | 4750 |
|  | TTAGCTGAAA | TAGAGTAGGT | TGCTTGAAAC | GAAAGCCACG | TCTGGAAAAT | 4800 |
|  | TTCTTATTGC | TTAGTAGTTG | TGACGTCACC | ATATACACAC | AAAATAATGT | 4850 |
|  | GTATGCATGC | GTTCAGCTG | TGTATATATA | CATGCACACA | CTCGCATTAT | 4900 |
|  | GAAAACGATG | ACGAGCAACG | GAACAGGTTT | CTCAACTACC | TTTGTTCCTG | 4950 |
|  | TTCTTCGCT | TTCCTTTGTT | CCAATATTCG | TAGAGGGTTA | ATAGGGGTTT | 5000 |
|  | CTCAACAAAG | TTGGCGTCGA | TAAATAAGTT | TCCCATTTTT | ATTCCCCAGC | 5050 |
|  | CAGGAAGTTA | GTTCAATAG | TTTTGTAATT | TCAACGAAAC | TCATTTGATT | 5100 |
|  | TCGTACTAAT | TTTCCACATC | TCTATTTTGA | CCCGCAGAAT | AATCCAAAAT | 5150 |
|  | GCAGATCGGG | GATCCCACCC | CACCCAAGAA | GAAGCGCAAG | GTGGAGGACG | 5200 |
|  | ATCCCGTCGT | TTTACAACGT | CGTGACTGGG | AAAACCCTGG | CGTTACCCAA | 5250 |
|  | CTTAATCGCC | TTGCAGCACA | TCCCCCTTTC | GCCAGCTGGC | GTAATAGCGA | 5300 |
|  | AGAGGCCCGC | ACCGATCGCC | CTTCCCAACA | GTTGCGGTCG | ACTCTAGAGG | 5350 |
|  | ATCCCCGGGA | TCCACCGGTC | GCCACCATGG | TGAGCAAGGG | CGAGGAGCTG | 5400 |

Fig. 6c

```
            10         20         30         40         50
     1234567890 1234567890 1234567890 1234567890 1234567890
     TTCACCGGGG TGGTGCCCAT CCTGGTCGAG CTGGACGGCG ACGTAAACGG   5450
     CCACAAGTTC AGCGTGTCCG GCGAGGGCGA GGGCGATGCC ACCTACGGCA   5500
     AGCTGACCCT GAAGTTCATC TGCACCACCG GCAAGCTGCC CGTGCCCTGG   5550
     CCCACCCTCG TGACCACCCT GACCTACGGC GTGCAGTGCT TCAGCCGCTA   5600
     CCCCGACCAC ATGAAGCAGC ACGACTTCTT CAAGTCCGCC ATGCCCGAAG   5650
     GCTACGTCCA GGAGCGCACC ATCTTCTTCA AGGACGACGG CAACTACAAG   5700
     ACCCGCGCCG AGGTGAAGTT CGAGGGCGAC ACCCTGGTGA ACCGCATCGA   5750
     GCTGAAGGGC ATCGACTTCA AGGAGGACGG CAACATCCTG GGGCACAAGC   5800
     TGGAGTACAA CTACAACAGC CACAACGTCT ATATCATGGC CGACAAGCAG   5850
     AAGAACGGCA TCAAGGTGAA CTTCAAGATC CGCCACAACA TCGAGGACGG   5900
     CAGCGTGCAG CTCGCCGACC ACTACCAGCA GAACACCCCC ATCGGCGACG   5950
     GCCCCGTGCT GCTGCCCGAC AACCACTACC TGAGCACCCA GTCCGCCCTG   6000
     AGCAAAGACC CCAACGAGAA GCGCGATCAC ATGGTCCTGC TGGAGTTCGT   6050
     GACCGCCGCC GGGATCACTC TCGGCATGGA CGAGCTGTAC AAGTAAAGCG   6100
     GCCGCGACTC TAGATCATAA TCAGCCATAC CACATTTGTA GAGGTTTTAC   6150
     TTGCTTTAAA AAACCTCCCA CACCTCCCCC TGAACCTGAA ACATAAAATG   6200
     AATGCAATTG TTGTTGTTAA CTTGTTTATT GCAGCTTATA ATGGTTACAA   6250
     ATAAAGCAAT AGCATCACAA ATTTCACAAA TAAAGCATTT TTTCACTGC   6300
     ATTCTAGTTG TGGTTTGTCC AAACTCATCA ATGTATCTTA AGGCGTAAAT   6350
     TGTAAGCGTT AATATTTTGT TAAAATTCGC GTTAAATTTT TGTTAAATCA   6400
     GCTCATTTTT TAACCAATAG GCCGAAATCG GCAAAATCCC TTATAAATCA   6450
     AAAGAATAGA CCGAGATAGG GTTGAGTGTT GTTCCAGTTT GGAACAAGAG   6500
     TCCACTATTA AAGAACGTGG ACTCCAACGT CAAAGGGCGA AAAACCGTCT   6550
     ATCAGGGCGA TGGCCCACTA CGTGAACCAT CACCCTAATC AAGTTTTTTG   6600
     GGGTCGAGGT GCCGTAAAGC ACTAAATCGG AACCCTAAAG GGAGCCCCCG   6650
     ATTTAGAGCT TGACGGGGAA AGCCGGCGAA CGTGGCGAGA AAGGAAGGGA   6700
     AGAAAGCGAA AGGAGCGGGC GCTAGGGCGC TGGCAAGTGT AGCGGTCACG   6750
     CTGCGCGTAA CCACCACACC CGCCGCGCTT AATGCGCCGC TACAGGGCGC   6800
     GTCAGGTGGC ACTTTTCGGG GAAATGTGCG CGGAACCCCT ATTTGTTTAT   6850
     TTTTCTAAAT ACATTCAAAT ATGTATCCGC TCATGAGACA ATAACCCTGA   6900
     TAAATGCTTC AATAATATTG AAAAGGAAG AGTCCTGAGG CGGAAAGAAC   6950
     CAGCTGTGGA ATGTGTGTCA GTTAGGGTGT GGAAAGTCCC CAGGCTCCCC   7000
     AGCAGGCAGA AGTATGCAAA GCATGCATCT CAATTAGTCA GCAACCAGGT   7050
     GTGGAAAGTC CCAGGCTCC CCAGCAGGCA GAAGTATGCA AAGCATGCAT   7100
     CTCAATTAGT CAGCAACCAT AGTCCCGCCC CTAACTCCGC CCATCCGCC   7150
     CCTAACTCCG CCCAGTTCCG CCCATTCTCC GCCCCATGGC TGACTAATTT   7200
```

Fig. 6d

|  | 10 | 20 | 30 | 40 | 50 |  |
| --- | --- | --- | --- | --- | --- | --- |
|  | 1234567890 | 1234567890 | 1234567890 | 1234567890 | 1234567890 |  |
| TTTTTATTTA | TGCAGAGGCC | GAGGCCGCCT | CGGCCTCTGA | GCTATTCCAG | | 7250 |
| AAGTAGTGAG | GAGGCTTTTT | TGGAGGAACC | ATTGTGGGAA | CCGTGCGATC | | 7300 |
| AAACAAACGC | GAGATACCGG | AAGTACTGAA | AAACAGTCGC | TCCAGGCCAG | | 7350 |
| TGGAACATC | GATGTTTGT | TTTGACGGAC | CCCTTACTCT | CGTCTCATAT | | 7400 |
| AAACCGAAGC | CAGCTAAGAT | GGTATACTTA | TTATCATCTT | GTGATGAGGA | | 7450 |
| TGCTTCTATC | AACGAAAGTA | CCGGTAAACC | GCAAATGGTT | ATGTATTATA | | 7500 |
| ATCAAACTAA | AGGCGGAGTG | GACACGCTAG | ACCAAATGTG | TTCTGTGATG | | 7550 |
| ACCTGCAGTA | GGAAGACGAA | TAGGTGGCCT | ATGGCATTAT | TGTACGGAAT | | 7600 |
| GATAAACATT | GCCTGCATAA | ATTCTTTTAT | TATATACAGC | CATAATGTCA | | 7650 |
| GTAGCAAGGG | AGAAAAGGTC | CAAGTCGCA | AAAAATTTAT | GAGAAACCTT | | 7700 |
| TACATGAGCC | TGACGTCATC | GTTTATGCGT | AAGCGTTTAG | AAGCTCCTAC | | 7750 |
| TTTGAAGAGA | TATTTGCGCG | ATAATATCTC | TAATATTTTG | CCAAATGAAG | | 7800 |
| TGCCTGGTAC | ATCAGATGAC | AGTACTGAAG | AGCCAGTAAT | GAAAAAACGT | | 7850 |
| ACTTACTGTA | CTTACTGCCC | CTCTAAAATA | AGGCGAAAGG | CAAATGCATC | | 7900 |
| GTGCAAAAAA | TGCAAAAAAG | TTATTGTCG | AGAGCATAAT | ATTGATATGT | | 7950 |
| GCCAAAGTTG | TTTCTGACTG | ACTAATAAGT | ATAATTTGTT | TCTATTATGT | | 8000 |
| ATAAGTTAAG | CTAATTACTT | ATTTTATAAT | ACAACATGAC | TGTTTTTAAA | | 8050 |
| GTACAAAATA | AGTTTATTTT | TGTAAAGAG | AGAATGTTTA | AAGTTTTGT | | 8100 |
| TACTTTATAG | AAGAAATTTT | GAGTTTTGT | TTTTTTTTAA | TAAATAAATA | | 8150 |
| AACATAAATA | AATTGTTTGT | TGAATTTATT | ATTAGTATGT | AAGTGTAAAT | | 8200 |
| ATAATAAAAC | TTAATATCTA | TTCAAATTAA | TAAATAAACC | TCGATATACA | | 8250 |
| GACCGATAAA | ACACATGCGT | CAATTTTACG | CATGATTATC | TTTAACGTAC | | 8300 |
| GTCACAATAT | GATTATCTTT | CTAGGGTTAA | ATAATAGTTT | CTAATTTTTT | | 8350 |
| TATTATTCAG | CCTGCTGTCG | TGAATACCGT | ATATCTCAAC | GCTGTCTGTG | | 8400 |
| AGATTGTCGT | ATTCTAGCCT | TTTTAGTTTT | TGCTCATCG | ACTTGATATT | | 8450 |
| GTCCGACACA | TTTTCGTCGA | TTTGCGTTTT | GATCAAAGAC | TTGAGCAGAG | | 8500 |
| ACACGTTAAT | CAACTGTTCA | AATTGATCCA | TATTAACGAT | ATCAACCCGA | | 8550 |
| TGCGTATATG | GTGCGTAAAA | TATATTTTTT | AACCCTCTTA | TACTTTGCAC | | 8600 |
| TCTGCCGTTAA | TACGCGTTCG | TGTACAGACG | TAATCATGTT | TTCTTTTTTG | | 8650 |
| GATAAAACTC | CTACTGAGTT | TGACCTCATA | TTAGACCCTC | ACAAGTTGCA | | 8700 |
| AAACGTGGCA | TTTTTTACCA | ATGAAGAATT | TAAAGTTATT | TTAAAAAATT | | 8750 |
| TCATCACAGA | TTTAAAGAAG | AACCAAAAAT | TAAATTATTT | CAACAGTTTA | | 8800 |
| ATCGACCAGT | TAATCAACGT | GTACACAGAC | GCGTCGGCAA | AAAACACGCA | | 8850 |
| GCCCGACGTG | TTGGCTAAAA | TTATTAAATC | AACTTGTGTT | ATAGTCACGG | | 8900 |
| ATTTGCCGTC | CAACGTGTTC | CTCAAAAAGT | TGAAGACCAA | CAAGTTTACG | | 8950 |
| GACACTATTA | ATTATTTGAT | TTTGCCCCAC | TTCATTTTGT | GGGATCACAA | | 9000 |

FIG. 6e

|  | 10 | 20 | 30 | 40 | 50 |  |
|---|---|---|---|---|---|---|
|  | 1234567890 | 1234567890 | 1234567890 | 1234567890 | 1234567890 |  |
|  | TTTTGTTATA | TTTTAAACAA | AGCTTGGCAC | TGGCCGTCGT | TTTACAACGT | 9050 |
|  | CGTGACTGGG | AAAACCCTGG | CGTTACCCAA | CTTAATCGCC | TTGCAGCACA | 9100 |
|  | TCCCCCTTTC | GCCAGCTGGC | GTAATAGCGA | AGAGGCCCGC | ACCGATCGCC | 9150 |
|  | CTTCCCAACA | GTTGCGCAGC | CTGAATGGCG | AATGGCGCCT | GATGCGGTAT | 9200 |
|  | TTCTCCTTA | CGCATCTGTG | CGGTATTTCA | CACCGCATAT | GGTGCACTCT | 9250 |
|  | CAGTACAATC | TGCTCTGATG | CCGCATAGTT | AAGCCAGCCC | CGACACCCGC | 9300 |
|  | CAACACCCGC | TGACGCGCCC | TGACGGGCTT | GTCTGCTCCC | GGCATCCGCT | 9350 |
|  | TACAGACAAG | CTGTGACCGT | CTCCGGGAGC | TGCATGTGTC | AGAGGTTTTC | 9400 |
|  | ACCGTCATCA | CCGAAACGCG | CGA |  |  | 9423 |

FIG. 6 f

PIGGYBAC TRANSFORMATION SYSTEM

BACKGROUND OF INVENTION

1. Field of the Invention

This invention relates to a transformation system that includes a gene transfer vector containing a modified piggyBac transposon (pB) and having the insertion of a marker construct containing an enhanced green fluorescent protein gene (EGFP) linked to a polyubiquitin promoter gene and a nuclear localizing sequence. The invention further relates to a helper vector containing a heat shock protein gene and to methods for using this system to transform eukaryotic cells as well as transgenic organisms produced using the system, especially insect cells and insects, respectively.

2. Description of the Related Art

The piggyBac transposable element from the cabbage looper moth, Trichoplusia ni (Cary et al., Virology, Volume 161, 8–17, 1989) has been shown to be an effective gene-transfer vector in the Mediterranean fruit fly, Ceratitis capitata (Handler et al., Proc. Natl. Acad. Sci. USA, Volume 95, 7520–7525, 1998). Use of an unmodified transposase helper under piggyBac promoter regulation indicates that piggyBac retains autonomous function in the medfly, since transcriptional regulation was maintained, as well as enzymatic activity. This observation was unique since all other successful insect germline transformations had been limited to dipteran species using vectors isolated from the same or another dipteran. The initial transformation of medfly (Loukeris et al., Science, Volume 270, 2002–2005, 1995) used the Minos vector from Drosophila hydei (Franz & Savakis, Nucl. Acids Res., Volume 19, 6646, 1991), and Aedes aegypti has been transformed from Hermes (Jasinskiene et al., Proc. Natl. Acad. Sci. USA, Volume 95, 3743–3747, 1998) from Musca domestica (Warren et al., Genet. Res. Camb., Volume 64, 87–97, 1994) and mariner (Coates et al., Proc. Natl. Acad. Sci. USA, Volume 95, 3748–3751, 1998) from Drosophila mauritiana (Jacobson et al., Proc. Natl. Acad. Sci. USA, Volume 83, 8684–8688, 1986). Drosophila melanogaster has been transformed as well by Hermes (O'Brochta et al., Insect Biochem. Molec. Biol., Volume 26, 739–753, 1996) mariner (Lidholm et al., Genetics, Volume 134, 859–868, 1993), Minos (Franz et al., Proc. Natl. Acad. Sci. USA, Volume 91, 4746–4750, 1994) and by the P and hobo transposons originally discovered in its own genome (Rubin and Spradling, 1989; Blackman et al., EMBO J., Volume 8, 211–217, 1989). Drosophila virilis also has been transformed by hobo (Lozovskaya et al., Genetics, Volume 143, 365–374, 1995; Gomez & Handler, Insect Mol. Biol., Volume 6, 1–8, 1997) and mariner (Lohe et al., Genetics, Volume 143, 365–374, 1996). While the restriction to dipteran vectors is due in part to the limited number of transposon systems available from non-dipteran species, phylogenetic limitations on transposon function is not unexpected considering the deleterious effects functional transposons may have on a host genome. This is, indeed, reflected by the high level of regulation placed on transposon movement among species, among strains within a host species, and even among cell types within an organism (Berg & Howe, Mobile DNA, American Society for Microbiology, Washington, D.C. 1989).

The ability of piggyBac to function in several dipteran species will be supportive of its use in a wider range of insects, if not other organisms. Most other vector systems function optimally, or have been only tested with their helper transposase under hsp70 promoter regulation. The transposition efficiency of most vectors has been also found to be influenced by the amount of internal DNA inserted, the position of this DNA within the vector, and the amount of subterminal DNA remaining in the vectors.

The widespread use of piggyBac will be limited by the availability of easily detectable and unambiguous transformant markers. Most Drosophila transformations, as well as the few nondrosophilid transformations reported have depended on transformant selection by rescue of a mutant visible phenotype, usually eye pigmentation (Ashburner et al., Insect Mol. Biol., Volume 7, 201–213, 1998). Unfortunately, most insect species have neither visible mutant strains, nor the cloned DNA for the wild type allele of the mutation, and these species require use of new dominant-acting marker genes that confer, preferably, a visible phenotype.

The present invention, discussed below, provides a system that includes vectors for transforming eukaryotic cells, derived from piggyBac transposons that are different from related art vectors. Furthermore, the present invention increases the transformation frequency by about eight-fold compared to other piggyBac transformation systems.

SUMMARY OF THE INVENTION

It is therefore an object of the present invention to provide a transformation system contains a vector that includes DNA derived from a piggyBac transposon element that allows for the almost precise excision of at least a second DNA sequence that is heterologous and included in the construct and insertion of at least said second heterologous DNA sequence into eukaryotic cells after introduction of the transformation construct containing said first and at least a second DNA into said cell that is then used to form a transgenic organism wherein said transgenic organism is detectable under ultraviolet light.

Another object of the present invention is to provide a transformation system that includes a vector containing a modified piggyBac sequence, a sequence for marker expression linked to a polyubiquitin promoter and a nuclear localizing sequence and a helper vector including a heat shock protein gene wherein said system causes an increase in transformation frequency compared to other piggyBac transformation systems.

A still further object of the present invention is to provide a vector containing a modified piggyBac sequence and an enhanced green fluorescent protein sequence linked to a polyubiquitin promoter and a nuclear localizing sequence.

A still further object of the present invention is to provide a vector that is useful in transforming eukaryotic cells having the sequence SEQ ID No 6.

Another object of the present invention is to provide a transgenic organism that is detectable under ultraviolet light.

A further object of the present invention is to provide a eukaryotic transgenic organism that has been transformed using a transformation system that includes vector containing a modified piggyBac sequence, an enhanced green fluorescent protein gene linked to a polyubiquitin promoter and a nuclear localizing sequence, and a helper vector containing a heat shock protein gene promoter.

A still further object of the present invention is to provide a transgenic insect that has been transformed using a vector having the sequence SEQ ID NO 6.

Further objects and advantages of the present invention will become apparent from the following description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4(a) is a schematic (not to scale) of the vector insertion in the host plasmid showing the approximate location of the restriction sites and primers used for PCR. Forward (F) and reverse (R) primers are numbered according to their nucleotide position in piggyBac. The piggyBac sequence is shown in gray surrounded by the TTAA (SEQ ID NO 1) duplicated insertion site, the mini-white marker gene is white, and chromosomal sequence is hatched. FIG. 4(b) shows the piggyBac insertion site sequence in p3E1.2 (SEQ ID NOs 7 and 8), and the proximal insertion site sequences (SEQ ID NOs 9 and 10, 11 and 12, and 13 and 14) for three of the transformant sublines.

FIGS. 6a–6f show SEQ ID NO 6 for pB[PUb-nls-EGFP] #257.

DETAILED DESCRIPTION OF THE INVENTION

The present invention is an effective transformation system for producing transgenic organisms, especially transgenic insects. The identification and isolation of an autonomous piggyBac transposon enables transformation of cells and the production of transgenic organisms wherein DNA capable of being expressed in the transformed cell or transgenic organism is excised from a transformation construct and inserted into the genome of a cell used to produce a transgenic organism U.S. patent application Ser. No. 08/844,274, now U.S. Pat. No. 6,218,185, issued April 17, 2001; herein incorporated by reference). The term cell for the purposes of this invention includes any cell capable of being transformed by the transformation construct of the present invention and preferably includes any eukaryotic cell. The term organism for the purposes of the present invention includes any unicellular or multicellular living entity capable of being transformed by the transformation construct of the present invention and preferably includes multicellular eukaryotes. More preferably, the cell or organism is an insect cell or an insect.

The present invention utilizes the transposon machinery of the TTAA (SEQ ID NO 1) specific transposons to excise and insert a targeted functional heterologous DNA sequence into the genome of the host cell. The resulting transformed cell or group of cells are stable transformants that are then used to make a transgenic organism, using techniques known to the skilled artisan, that will pass the introduced gene to all subsequent progeny. The targeted functional heterologous DNA for purposes of this invention is any heterologous DNA capable of being expressed in a host cell and/or a transgenic organism.

Figure 5:
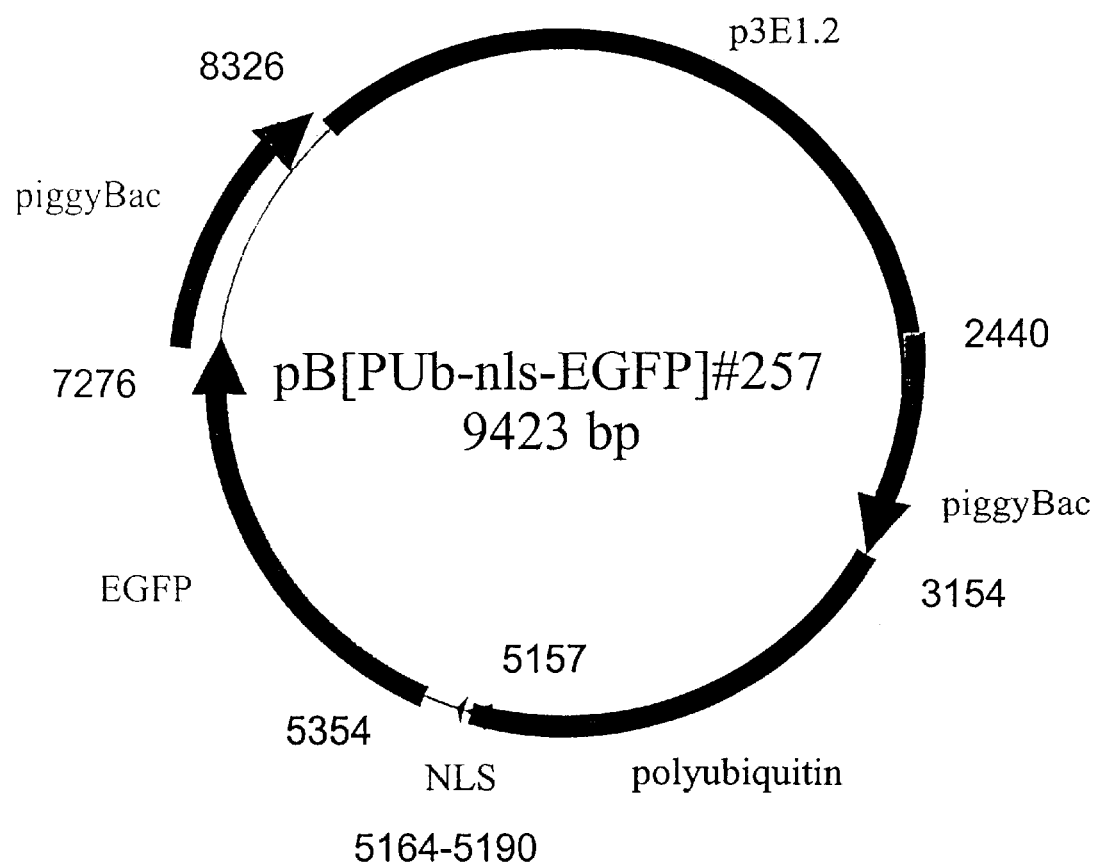
FIG. 5 shows a circular map of the vector pB[PUb-nls-EGFP] #257.
Figure 7A:
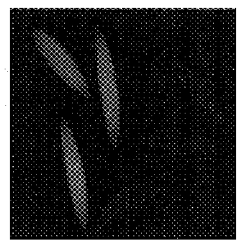
FIG. 7(a) is a photomicrograph showing GFP expression in Anastrepha suspensa transformed with piggyBac/PUb-nls-EGFP at embryo stages. Under UV light, transformants exhibit bright green fluorescence, with wild-type non-transformants exhibiting muted yellow autofluourescence (digital images taken with Leica MZ-12 fluorescence microscope and SPOT-1 CCD camera).
Figure 7B:
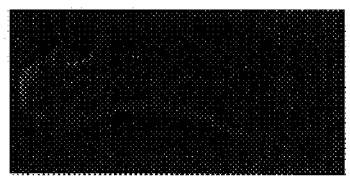
FIGS. 7(b) and 7(c) are photomicrographs showing GFP expression in Anastrepha suspensa transformed with piggyBac/PUb-nls-EGFP at larval stages. 7(b) is a wild-type non-transformant and 7c is a transformant. Under UV light, transformants exhibit bright green fluorescence, with wild-type non-transformants exhibiting muted yellow autofluourescence (digital images taken with Leica MZ-12 fluorescence microscope and SPOT-1 CCD camera).
Figure 7C:
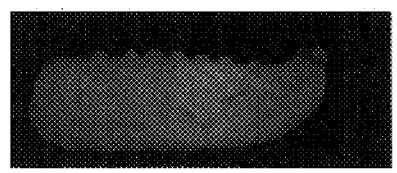
Figure 7D:
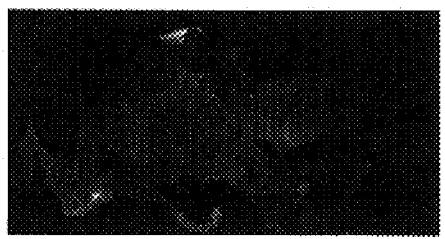
FIGS. 7(d) and 7(e) are photomicrographs showing GFP expression in Anastrepha suspensa transformed with piggyBac/PUb-nls-EGFP at adult stages. 7(d) is a wild-type non-transformant and 7(e) is a transformant. Under UV light, transformants exhibit bright green fluorescence, with wild-type non-transformants exhibiting muted yellow autofluourescence (digital images taken with Leica MZ-12 fluorescence microscope and SPOT-1 CCD camera).
Figure 7E:
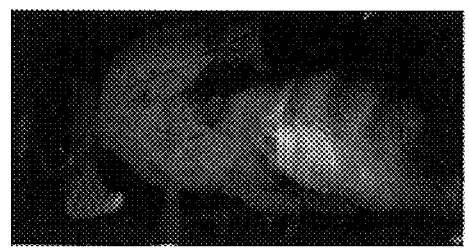
Figure 8A:
FIGS. 8(a)–8(e) are eye color phenotypes of Bactrocera dorsalis wild-type (+) and white eye (WE) host strain and the Bd[pBCcw] transformant lines 61,115, and 137.
Figure 8B:
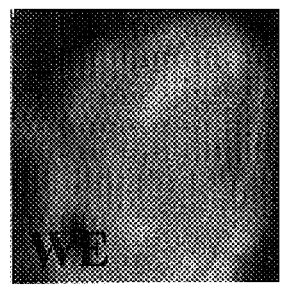
Figure 8C:
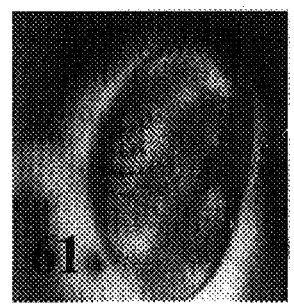
Figure 8D:
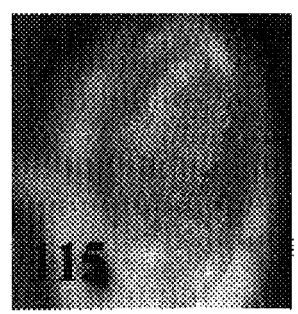
Figure 8E:
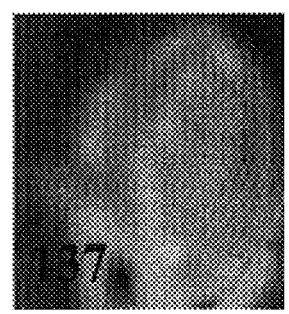

The transformation system of the present invention includes a vector, such as, for example, pB[PUb-nls-EGFP] (FIGS. 5 and 6), that includes a modified piggyBac transposon (pB), a marker construct that includes the enhanced green fluorescent protein gene (EGFP) linked to the promoter region of the Drosophila melanogaster polyubiquitin (PUb) gene and the nuclear localizing sequence (nls) of the SV40 virus. This vector can be used to transform and detect transgenic organisms based on expression of the green fluorescent protein marker under ultraviolet light. After chromosomal integration and inheritance of the vector, expression of green fluorescent protein occurs in all cell types, is intense, strongly localized to nuclei, and continues to be detectable under ultraviolet light even after death of the organism. The novel features of this vector includes its construction that deletes about 748 bp of internal piggyBac sequence without diminishing its function, and the function of the polyubiquitin promoter in a nondrosophilid species. This has utility as a broadly based method for the creation and selection of transgenic organisms, and as a genetic marker for detecting and tracking transgenic insects used in field release programs (FIG. 5).

GFP expressivity is critical for nondrosophilid species not amenable to mutant-rescue, it also widens the possibility for using the dominant expression of GFP as a primary transformant marker in many Drosophila lines not already carrying the white or rosy mutations, or for screens requiring selection in early development. Though vectors carrying white and gfp have been tested previously, the transformations used only white as the transformant selection, with GFP assessed secondarily for specific spatial or developmental expression (Davis et al., Devel. Biol., Volume 170, 726–729, 1995; Wang & Hazelrigg, Nature, Volume 369, 400–403, 1994).

The transformation system of the present invention also includes a piggyBac transposase helper plasmid, pBΔSac, having its' 5' terminus deleted as described by Handler et al. (1998, supra; herein incorporated by reference). A new transposase helper under heat-shock promoter regulation was created by the isolation of the 457 bp XbaI-XmnI 5' nontranslated sequence from the hsp70 gene (Lis et al., Cell, Volume 35, 403–410, 1983, herein incorporated by reference). The heat-shock regulated helper increases the transformation frequency by eight-fold in Drosophila, indicating that the piggyBac system could be as effective as routinely used systems such as P and hobo that have been thus far inactive in nondrosophilids (O'Brochta & Atkinson, Insect Biochem. Molec. Biol., Volume 26, 739–753, 1996).

The creation of a transformed cell requires that the vector containing the functional heterologous DNA first be physically placed within the host cell. Current transformation procedures utilize a variety of techniques to introduce DNA into a cell. In one form of transformation for vertebrate systems, the DNA is microinjected directly into embryos through the use of micropipettes. Alternatively, high velocity biolistics can be used to propel small DNA associated particles into the cell. In another form, the cell is permeablized by the presence of polyethylene glycol, thus allowing DNA to enter the cell through diffusion. DNA can also be introduced into a cell by fusing protoplasts with other entities that contain DNA. These entities include minicells, cells, lysosomes, or other fusible lipid-surfaced bodies. Electroporation is also an accepted method for introducing DNA into a cell. In this technique, cells are subject to electrical impulses of high field strength that reversibly permeabilizes biomembranes, allowing the entry of exogenous DNA sequences. One preferred method of introducing the transformation system of the present invention into insect embryos, in accordance with the present invention, is to microinject fertilized eggs with the vectors of the present invention. The DNA sequence flanked by the transposon inverted repeats will be inserted into the genome of some of the germ cells of the fertilized egg during development of the organism. This DNA will then be passed on to all of the progeny cells to produce transgenic organisms. The microinjection of eggs to produce transgenic animals has been previously described and utilized to produce transformed mammals and insects (Rubin et al., Science, Volume 218, 384–393, 1982; Hogan et al., Manipulating the Mouse Embryo: A Laboratory Manual, Cold Spring Harbor Laboratory Press, Plainview, N.Y., 1986; Morgan et al., Annu. Rev. Biochem., Volume 62, 191–217, 1993; Spradling, A.C., In: Drosophila: A Practical Approach, ed. D.B. Roberts, Oxford: IRL Press, 175–197, 1986; all herein incorporated by reference). Accordingly, a method of producing stably transformed insects includes the step of microinjecting the transformation constructs of the present invention comprising the inverted repeats of a TTAA specific transposon and a helper construct into a cell, preferably a fertile insect egg. This is followed by incubation in an oxygenated and humidified tissue culture chamber at about 22–23° C. for about 3–6 hours. Injected cells or eggs are then heat shocked at about 37°–41° C., about 39° C. preferred, for about 1 hour. The resulting transformed cells or transgenic organisms have exogenous DNA inserted into the genomic DNA at the sequence TTAA.

Transformed cells and/or transgenic organisms can be selected from untransformed cells and/or non-transgenic organisms by ultraviolet light since the transformation system includes an enhanced green fluorescent protein gene that produces an altered visible phenotype under ultraviolet light.

Using standard techniques known to those familiar with the field, techniques such as, for example, Southern blotting and polymerase chain reaction, DNA can be isolated from transformed cells and/or transgenic insects to confirm that the introduced DNA has been inserted.

Genetic modification of insects with new genetic elements provides a means to control populations of agriculturally pestiferous or beneficial insects. The ability to control pest insects through genetically based sterile insect programs or genetically introduced targeted conditional susceptibilities will result in significant cost savings to agribusiness. This technology can also be used for detection and monitoring of insect populations and infestations where piggyBac transgenic insects are present in the population. In addition, introduction of genes that impart resistance to chemicals (including herbicides, pesticides, and insecticides) can improve the efficacy of beneficial insects. Each of these applications will result in more efficient pest control programs.

Enhancing the resistance of beneficial insects to pesticides will enhance the efficacy of the beneficial insects and may allow for the simultaneous use of chemical control and biological control of pests. Some of the beneficial insects that would make good candidates for such transformations include *Hymenopteran parasitoids* of Heliothis spp.: *Micropilitis croceips* and *Cardiochiles nigriceps*; *Hymenopteran parasitoid* of Diamondback moth, *Plutella xylostella: Diadegma insolare*; *Hymenopteran parasitod* of the Indianmeal moth, *Plodia interpunctella: Bracon hebitor*; and *Hemipteran predators: Xylocoris flavipes, Podisus maculatus*.

The following examples are intended only to further illustrate the invention and are not intended to limit the scope of the invention as described by the claims. *Drosophila melanogaster* white strain w[m], was used in the following examples as a model system for transformation system studies using the vectors of the present invention. *D. melanogaster* and transformant progeny were maintained at about 23–25° C. on standard cornmeal-yeast-molasses media.

EXAMPLE 1

The piggyBac transposase helper plasmid, pBΔSac, having its 5' terminus deleted as described previously (Handler et al., 1998; supra, herein incorporated by reference). pBΔSac was created by digestion of p3E1.2 (U.S. patent application Ser. No. 08/844,274, now U.S. Pat. No. 6,218, 185, issued Apr. 17, 2001)with SacI and religation, that deletes the 5' piggyBac terminal sequences but maintains the putative piggyBac promoter region. A transposase helper under heat-shock promoter regulation was created by isolation of the 457 bp XbaI-XmnI 5' nontranslated sequence from the hsp70 gene (Lis et al., 1983, supra; herein incorporated by reference). The XbaI-XmnI fragment was blunted and ligated into the SacI-blunted site of pBΔSac to create phsp-pBac. This places the hsp70 promoter sequence upstream of the putative piggyBac promoter.

The pB[Dmw] vector was created by insertion of a *Drosophila melanogaster* mini-white gene (Pirrotta et al., EMBO J., Volume 4, 3501–3508, 1985; herein incorporated by reference) into the 3E1 piggyBac element within the 6.0 kb p3E1.2 plasmid (Cary et al., 1989, supra). The mini-white gene was isolated as a 4.2 kb EcoRI fragment, blunted and ligated into the p3E1.2 HpaI site. The inserted w gene interrupts the piggyBac open reading frame (ORF), but otherwise leaves the piggyBac element intact, with the respective promoters in opposite orientation. A piggyBac vector marked with w and gfp was created by initial construction of piggyBac marked with an enhanced gfp regulated by *D. melanogaster* polyubiquitin (PUb) promoter (Lee et al., Mol. Cell. Biol., Volume 8, 4727–4735, 1988; herein incorporated by reference) linked in-frame to the SV40 nuclear localizing sequence (nls) (Lanford et al., Mol. Cell. Biol., Volume 8, 2722–2729, 1986). The polyubiquitin-nls (PUb-nls) cassette from PUbnlsGFP (Davis et al., 1995, supra) was isolated as KpnI-SmaI fragment and inserted into the KpnI-SmaI cloning site of EGFP-1 (Clontech) (Cormack et al., Gene, Volume 173, 33–38, 1996; Yang et al., Nucleic Acid Res., Volume 24, 4592–4593, 1996). Polyubiquitin-nls-EGFP was then isolated as a 4.1 kb BglII-StuI fragment and ligated into the BglII-HpaI site of piggyBac within p3E1.2 to create pB[PUbnlsEGFP]. The BglII-HpaI digestion results in a 748 bp deletion within p3E1.2. The mini-white gene was then inserted into the unique BglII site by blunt-end cloning to create pB[Dmw, PUbnlsEGFP].

EXAMPLE 2

Embryo injections used standard procedures (Rubin & Spradling, Science, Volume 218, 348–353, 1982; herein incorporated by reference) with dechorionation achieved either manually or by 1.6% hypochlorite solution followed by about 2 washings in approximately 0.02% Triton-X 100 in water. Eggs were placed on double-stick tape, desiccated in room-air for about 10–15 minutes and submerged under Halocarbon 700 oil. Injections followed standard *Drosophila microinjection* procedures (Rubin and Spradling, Science, Volume 218, 348–353, 1982; herein incorporated by reference). DNA mixtures had vector:helper concentrations of about 600:400 μg/ml, respectively, in injection buffer (approximately 5 mM KCl; approximately 0.1 mM sodium phosphate; at about pH 6.8). Injected eggs were placed in an oxygenated and humidified tissue culture chamber at about 22–23° C. for about 3–6 hours, and phsp-pBac injected eggs were heat shocked at about 37° C. for about one hour. Hatched larvae were collected about 1–2 days later and placed on larval diet. Eclosed G0 male adults were mated either individually to about 2 or 3 w[m] virgin female adults, or in groups of about three females to about six males. G1 eggs were collected for two weeks. and reared under standard conditions that include maintaining the eggs at about 23–25° C. on standard cornmeal-yeast-molasses media (Ashburner et al., supra).

Green fluorescent protein (GFP) was observed at all developmental stages under a Leica MZ-12 stereozoom microscope using a mercury lamp and a ultraviolet longpass filter set (HQ 41012 FITC; Chroma) optimized for red-shifted GFP variants. Photographic documentation used an Olympus OM-4 camera and 400 ASA Fujichrome film with exposure times that were determined empirically.

Figure 1A:
FIG. 1(a) is a photograph of eye color phenotypes of Dm[pBw] transformants.

In the first of three transformation experiments, the piggyBac vector system was tested in *D. melanogaster* white strain using a helper transposase under piggyBac regulation (pBΔSac) and a vector marked solely with *D. melanogaster* mini-white gene (pB[Dmw]). A mixture of vector and helper plasmids at concentrations of about 600 and about 400 μg/ml, respectively, was injected into about 2,650 embryos from that about 418 larvae hatched with about 283 emerging as adults. (See Table 1 below). The G0 adults were backcrossed to w[m] flies in groups totaling about 111. Four of the G0 lines yielded G1 offspring having varying levels of eye pigmentation (FIG. 1). One line (F30) was sterile, and one line produced only white eye offspring, and therefore only two of the putative Dm[pBw] transformants were verified. One of these (F13) exhibited eye pigmentation only in females in several succeeding generations, suggesting that the integration caused a sex-linked lethal mutation. Presuming a fertility rate of about 50% (fertility rates are typically between about 40–60%; see below), an approximate transformation frequency of about 1–3% of fertile G0s was obtained.

In a second experiment, the pB[Dmw] vector was again tested but with a piggyBac transposase helper under *D. melanogaster* hsp70 (Lis et al., 1983 supra) promoter regulation (phsp-pBac). A vector/helper mixture, at a concentration of approximately 600/400 µg/ml was injected into about 1,940 embryos, of which about 247 larvae hatched, with about 122 emerging as adults (See Table 1, below). G0 adults were initially backcrossed in a total of about 49 groups to w[m] flies, after which they were individually mated to determine fertility. Of the about 98 surviving G0 flies, about 41 yielded offspring resulting in a fertility rate of about 42%. Of the 41 fertile G0 flies, 11 lines produced offspring having varying levels of eye coloration (FIG. 1) yielding a transformation frequency of about 26%. The number of G1 offspring from the G0 lines varied considerably, ranging from 1 G1 in lines M11 and F1, to 102 G1 flies in line M13.

Figure 1B:
FIG. 1(b) is a photograph of a w[m] host strain fly (top) and orange-eye Dm[pBw,gfp] transformant fly (bottom) under brightfield (left) and UV light (right).
Figure 1C:
FIG. 1(c) is a photograph of a w[m] host strain fly (top) and white-eye Dm[pBw,gfp] transformant fly (bottom) under brightfield (left) and UV light (right).

In a third experiment, the phsp-pBac helper was used, but with a piggyBac vector including the enhanced green fluorescent protein (gfp) marker gene in addition to the *D. melanogaster* white gene. This allowed the testing of a new gfp marker construct in transformants that could be primarily identified by white expression. Although expression of wild type GFP under polyubiquitin-nuclear localizing sequence regulation had been tested previously in *D. melanogaster* P transformants (Davis et al., 1995, supra), the vector of the present invention improves expression of GFP by using an enhanced GFP (EGFP-1) having a double mutation causing a reported increase in expression of up to about 35-fold (Cormack et al., 1996, supra; Yang et al., 1996, supra). The variant form is also optimized for mammalian codon usage and polyadenylation, and preliminary tests of the marker construct indicated transient GFP expression in both *Drosophila embryos* and dipteran and lepidopteran cell lines (A. M. Handler and R. A. Harrell, unpublished). The vector construct, pB[Dmw, PUbnlsEGFP], also allowed evaluation of piggyBac transformation with about a 10.0 kb vector, approximately 3.4 kb larger than previous vectors tested, and having about 748 bp of piggyBac DNA deleted (previous vectors retained all piggyBac DNA). As before, a mixture of about 600 µg/ml vector and about 400 µg/ml helper was injected into about 2147 embryos, of which about 412 larvae hatched, and about 218 emerged as adults (Table 1 below). G0 adults were backcrossed to w[m] flies in a total of about 90 mating groups, of which about 79 yielded offspring. Although white+ gene expression (eye pigmentation) was depended upon as the primary marker, G1 larvae and pupae were examined under UV for visible GFP expression, and seven of the G0 lines yielded fluorescent G1 larvae and pupae. Interestingly, as shown below in Table 2, upon adult emergence only six of the seven G0 lines yielded G1 offspring with observable eye color pigmentation. While about 70 G1 offspring in total exhibited observable green fluorescence, only about 27 of these flies exhibited a level of eye pigmentation that would have allowed their selection under normal screening procedures. In contrast, all of the G1 flies with eye color pigmentation expressed GFP. FIG. 1b shows a Dm[pBw, egfp] transformant having an orange eye color and GFP fluorescence, with no fluorescence observed in the w[m] host. FIG. 1c shows another transformant having a white eye phenotype indistinguishable from that in the w[m] host strain, but exhibiting an equal, if not greater level of GFP fluorescence compared to the orange eye transformant. Notably, fluorescence is quenched in the eye of the pigmented transformant, while it is easily visible in the white eye transformant. High magnification examination revealed a few pigmented ommatidia in some white eye G1 flies expressing GFP, though these would not have been normally detected. Based on selection by GFP expression and presuming about 50% fertility, an approximate transformation frequency of about 6–7% of fertile G0 flies is deduced.

An assessment of vector activity based on germline transformation frequency is a factor of both transposon mobility in the host embryo and levels of genomic position effect suppression of the marker gene, or stated more simply, the ability to visibly identify putative transformants. While position effect variegation and suppression of white expression in transformants is well established (Hazelrigg et al., Cell, Volume 64, 1083–1092, 1984; Pirotta et al., 1985, supra), the effect of complete marker suppression on transformation frequencies has not been assessed since such transformants have been only detected fortuitously after molecular analysis. The experiment using both the white and GFP markers proved the importance of position effects on marker expression convincingly, since GFP was readily detectable in 70 G1 flies, yet eye pigmentation was apparent in less than 40% of these. Under typical screening procedures these flies would not have been scored as transformants, though pigmentation in a few ommatidia in some flies could be detected at high magnification, and for a few lines, pigmentation was more apparent in subsequent generations. It is likely that expression of the white marker would have been improved by heat shock regulation, but nonetheless, GFP was easily detected in all the non-pigmented transformants, and strongly expressed in some. The influence of modifier genes on position effect variegation is complex, and target genes (or their promoters) are not equivalently affected (Bhadra et al., Genetics, Volume 150, 251–263, 1998). The polyubiquitin-gfp gene may be a target of position effect modifiers, but it is clearly less susceptible to suppression relative to white in terms of its expressed phenotype in the same chromosomal context. The data suggests that GFP is a more reliable visible marker than white, that portends well for its use as a general marker in other insects.

TABLE 1

Transformation Experiments.

| Expt. | vector/ helper | eggs injected | G0s mated | % fertility | No. G0 lines | No. G1 lines | transformant frequency |
|---|---|---|---|---|---|---|---|
| I | pB[Dmw]/ pBΔSac | 2,650 | 283 | nd | 4 | 11 | 0.01–0.03* |
| II | pB[Dmw]/ phsp-pBac | 1,940 | 122 | 42 | 11 | 266 | 0.26 |
| III | pB[Dmw, PUbnlsEGFP]/ phsp-pBac | 2,147 | 218 | nd | 7 | 70 | 0.06–0.07* |

*estimated frequency based on 50% fertility

TABLE 2

G1 white+ and GPR marker expression in Dm[pBw, gfp] transformants.

| G0 line | No. G1 | GFP | white+ | frequency white+ |
|---------|--------|-----|--------|------------------|
| M4      | 4      | 4   | 3      | 0.75             |
| M9      | 21     | 21  | 2      | 0.10             |
| M12     | 3      | 3   | 1      | 0.33             |
| M23     | 15     | 15  | 14     | 0.93             |
| M45     | 5      | 5   | 0      | 0                |
| M47     | 21     | 21  | 6      | 0.29             |
| F10     | 1      | 1   | 1      | 1.00             |
| Total   | 70     | 70  | 27     | 0.39             |

EXAMPLE III

Southern hybridization was performed to verify genomic transposition of the piggyBac vectors. Approximately 5–10 µg of genomic DNA was digested with indicated restriction enzymes and separated on about 0.8% agarose gels. DNA was stained with ethidium bromide, blotted to nylon filters and immobilized by ultraviolet irradiation. Hybridization probes were labeled with [$^{32}$P]-dCTP by random priming (Gibco BRL) according to the manufacturer's specifications. Probe DNA was generated from indicated piggyBac restriction fragments (see below) that were separated from p3E1.2, or the entire egfp gene from pEGFP-1 (Clontech) by agarose electrophoresis and gel-elution. Hybridizations were performed in phosphate buffer, approximately pH 7.5; about 1% BSA; about 7% SDS at about 65° C. with an initial wash in about 2×SSC; about 0.2% SDS at about room temperature and about two washes in about 1×SSC; about 0.1% SDS at about 55° C. for approximately 30 minutes. Autoradiography was performed by exposure of Kodak X-Omat film at about −90° C.

Genomic transposition of the piggyBac vectors was verified by Southern DNA hybridization. The basic strategy was to perform hybridizations to the 5' vector arm using the piggyBac SphI-HpaI or NsiI-HpaI fragment as probe, and the 3' vector arm using the HpaI-AseI or HpaI-NsiI fragment as probe. Using probes to both vector arms, internal fragments spanning most of the vector were detected. Hybridizations to the vector arms and adjacent chromosomal sequence indicate their presence in non-plasmid DNA and indicate the number of integrations, while internal hybridizations that yield known fragment sizes confirm vector integrity.

Figure 2A:
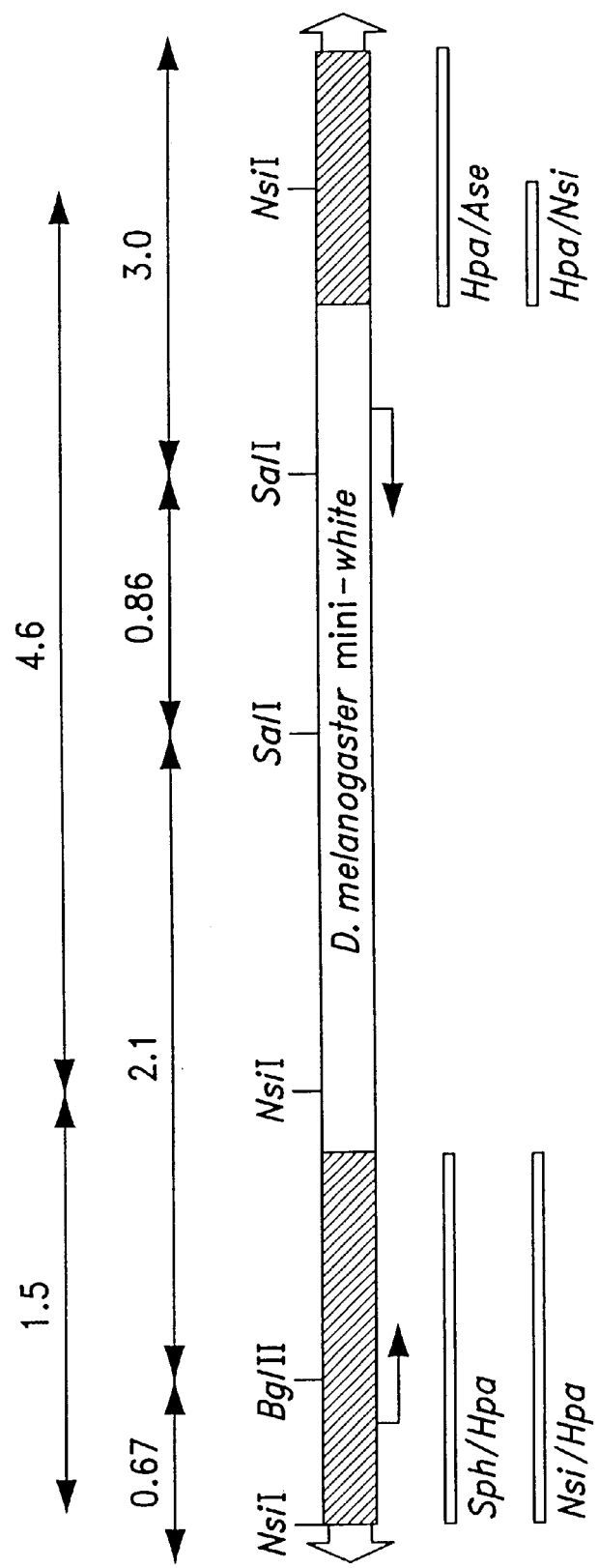
FIG. 2(a) is a schematic (not to scale) of the pB[Dmw] vector showing the BglII, SalI, and NsiI restriction sites used to digest the genomic DNA, and the probes used for hybridization (bars). Above the schematic are distances in kilobases used to calculate internal restriction fragment sizes and minimum sizes for junction fragments. PiggyBac vector sequences are shaded gray, and the mini-white marker gene is white.

For pB[Dmw] transformants, genomic DNA was initially digested with BglII and hybridized to the labeled Sph-Hpa piggyBac fragment, that detects both vector arms resulting in two bands for each integration (FIG. 2A). Each intact vector integration should result in one band greater than about 0.67 kb for the 5' arm, and one band greater than about 5.9 kb for the 3' arm. Since varying eye color phenotypes among G1 sublines was observed, and in some cases within G1 sublines, sublines having light orange, dark orange, or red eye coloration from the same G1 sublines were selected for hybridization analysis. For example, flies having differing phenotypes from lines M13-39, M19-90, and M19–91 were hybridized separately, but no difference in the number or sites of insertion were apparent. Of all the lines tested, all had single integrations except for two lines having two integrations (M13–39 and M19–91) and one line having three integrations (F14–63). All the lines with multiple integrations had dark orange or red eye color, though several lines with a single integration also shared these phenotypes. Hybridization patterns for the lines tested indicated that for most of the G0 lines, different integrations were transmitted to many of the G1 sibling offspring. For example, the three G1 sublines tested from both the M3 and M5 G0 lines all show different patterns indicating at least three independent integrations occurring in the two G0 germlines.

Figure 2B:
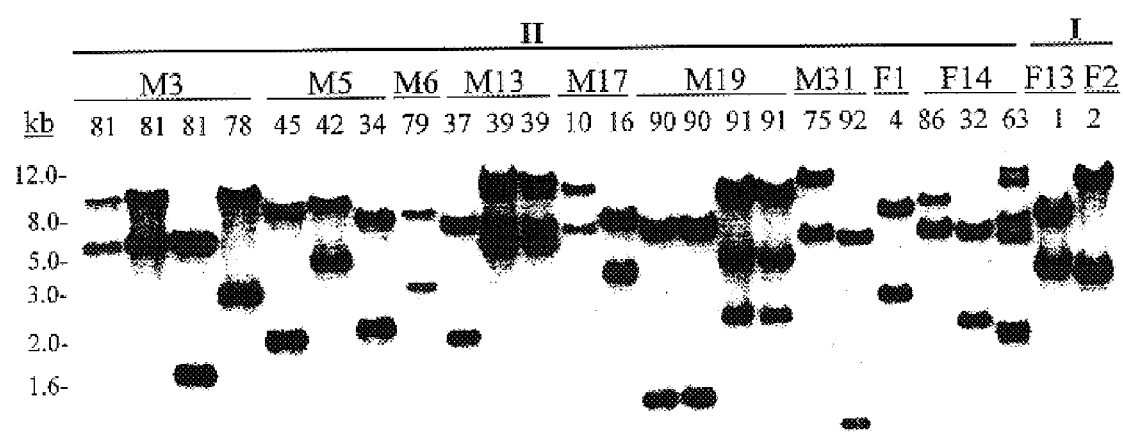
FIG. 2(b) shows an autoradiogram of a Southern DNA hybridization analysis of Dm[pBw] transformant sublines, and w[m] host strain control samples from transformants using the pBΔSac (experiment I) or phsp-pBac (experiment II) helpers using BglII digestion and Sph/Hpa piggyBac as probe. DNA size markers are shown to the left of the autoradiogram. M (male) and F (female) designations refer to G0 lines, with the numbers below referring to their respective G1 sublines.
Figure 2C:
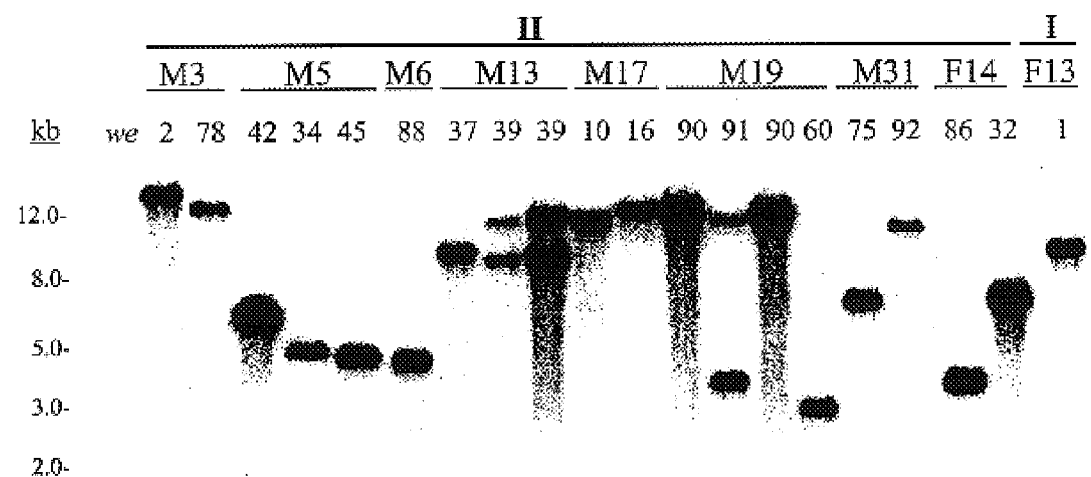
FIG. 2(c) shows a Southern DNA hybridization analysis of Dm[pBw] transformant sublines and w[m] host strain control samples from transformants, using the pBΔSac (experiment I) or phsp-pBac (experiment II) helpers ,using SalI digestion and Hpa/Ase piggyBac as probe. DNA size markers are shown to the left of the autoradiogram. M (male) and F (female) designations refer to G0 lines, with the numbers below referring to their respective G1 sublines.
Figure 2D:
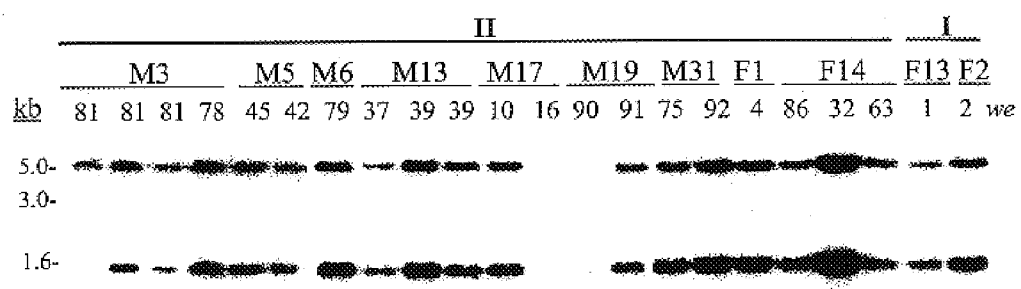
FIG. 2(d) shows a Southern DNA hybridization analysis of Dm[pBw] transformant sublines and w[m] host strain control samples from transformants, using the pBΔSac (experiment I) or phsp-pBac (experiment II) helpers, using NsiI digestion and Nsi/Hpa+Hpa/Nsi probes. DNA size markers are shown to the left of the autoradiogram. M (male) and F (female) designations refer to G0 lines, with the numbers below referring to their respective G1 sublines.

Genomic DNA digested with SalI and hybridized to HpaI-AseI probe yielded single bands greater than about 3.0 kb for each integration, and the number of integrations determined were consistent with the SphI-HpaI hybridizations (FIG. 2B). For all samples, NsiI digestion and hybridization to Nsi-HpaI and HpaI-NsiI probe yielded only about 1.5 kb and about 4.6 kb bands accounting for about 6.1 kb of the about 6.6 kb vector, indicating the same generally high level of vector integrity for all integrations tested.

Figure 3A:
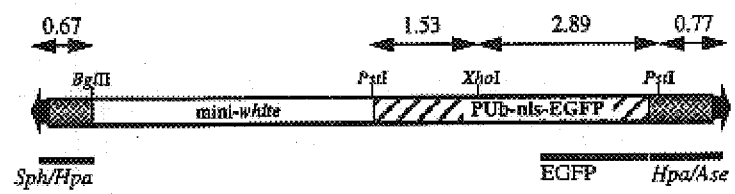
FIG. 3(a) is a schematic (not to scale) of the pB[Dmw, PUbnlsEGFP] vector showing the BglII, XhoI, and PstI restriction sites used to digest the genomic DNA, and the probes used for hybridization (bars). The Sph/Hpa piggyBac as probe contains 0.67 kb of vector sequence (SphI to BglII) with BglII to HpaI piggyBac sequence deleted from the vector. Above the schematic are distances in kilobases used to calculate internal restriciton fragment sizes and minimum sizes for junction fragments. PiggyBac vector sequences are shaded gray, the mini-white marker gene is white, and the EGFP marker gene is hatched.
Figures 3B, 3C:
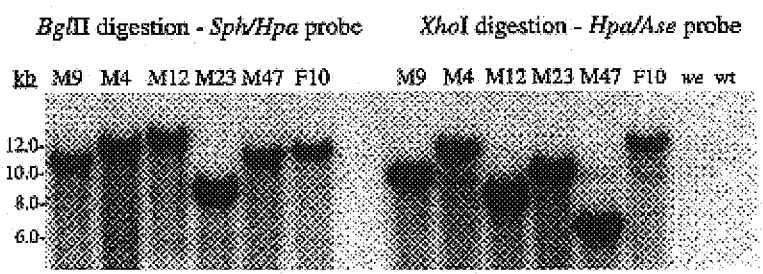
FIG. 3(b) is an autoradiogram of a Southern DNA hybridization analysis of Dm[pBw, gfp] transformant sublines, and wild type (wt) and w[m] host strain control samples using BglII digestion and Sph/Hpa piggyBac as probe. DNA size markers are shown to the left of the autoradiogram. M (male) and F (female) designations refer to G0 lines with selected G1 transformant progeny of samples.
FIG. 3(c) is an autoradiogram of a Southern DNA hybridization analysis of Dm[pBw, gfp] transformant sublines, and wild type (wt) and w[m] host strain control samples using XhoI digestion and Hpa/Ase piggyBac fragment as probe. DNA size markers are shown to the left of the autoradiogram. M and F designations refer to G0 lines with selected G1 transformant progeny of samples.
Figure 3D:
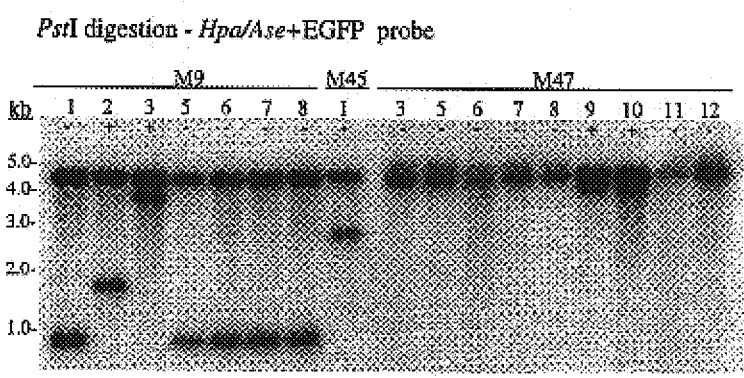
FIG. 3(d) is an autoradiogram of a Southern DNA hybridization analysis of Dm[pBw, gfp] transformant sublines, and wild type (wt) and w[m] host strain control samples using PstI digestion and Hpa/Ase piggBac fragment+EGFP DNA as probe. DNA size markers are shown to the left of the autoradiogram. M and F designations refer to G0 lines with specific G1 line numbers are given below, with the designation (+) for those expressing visible eye pigmentation and (−) for those having non-pigmented white eyes.

G1 sublines from six G0 lines transformed with the pB[Dmw, PUbnlsEGFP] vector were digested with either BglII and probed with SphI-HpaI piggyBac DNA for 5' vector arm analysis, or digested with XhoI and probed with HpaI-AseI piggyBac DNA for 3' arm analysis (FIG. 3A and 3B). Both hybridizations yielded one band for each sample, indicating single integrations having occurred in each line. NsiI restriction digests with NsiI-HpaI and HpaI-NsiI hybridizations yielded about 0.7 kb and about 0.8 kb bands indicating vector integrity for each integration (data not shown).

Two G0 lines, M9 and M47, yielded a high proportion of G1 flies expressing only GFP and white eyes, and line M45 that yielded only white eye transformants. These lines were analyzed by PstI digestion and hybridization to EGFP and Hpa-Ase. All lines shared the about 4.4 kb internal vector fragment, with an additional junction fragment from the 3' vector arm and adjacent insertion site chromosomal DNA. The M9 white eye lines all shared the same integration indicated by an about 0.9 kb junction fragment, and similarly the M47 white eye lines all shared the same 5.0 kb junction fragment. The pigmented lines M9-2 and M9-3 had different integrations from each other, and from their white eye sibling lines, and the pigmented lines M47-9 and M47-10 shared the same integration based on an about 4.0 kb junction fragment, but which differs from their white eye siblings. These hybridizations, and that for M45-1, proves that the white eye flies were transformed, and that white expression was likely influenced by differing insertion sites from their pigmented sibling lines.

EXAMPLE IV

To verify that piggyBac-mediated chromosomal transpositions had occurred, insertion sites were isolated by inverse PCR from sublines F1-2, M17-4 and M31-6, all having single integrations. Inverse PCR was performed as described previously (Handler et al., 1998, supra; herein incorporated by reference) using HaeIII digestions for 5' and 3' junctions and MspI digestion for 3' junctions. After about 4 hours digestion, restriction fragments were circularized by ligation at about 16° C. for about 16 hours. PCR was preformed on the circularized fragments by using primer sequences in opposite orientation within the piggyBac restriction site and terminus for each junction. For the 5' junction, the forward primer (572F) 5'-TCTTGACCTTGCCACAGAGG-3' (SEQ ID NO 2) and reverse primer (154R) 5'-TGACACTTACCGCATTGACA-3' (SEQ ID NO 3) were used. For the 3' junction the reverse primer (2118R) 5'-GTCAGTCCAGAAACAACTTTGGC-3' (SEQ ID NO 4) and the forward primer (2385F)

Figure 4A:
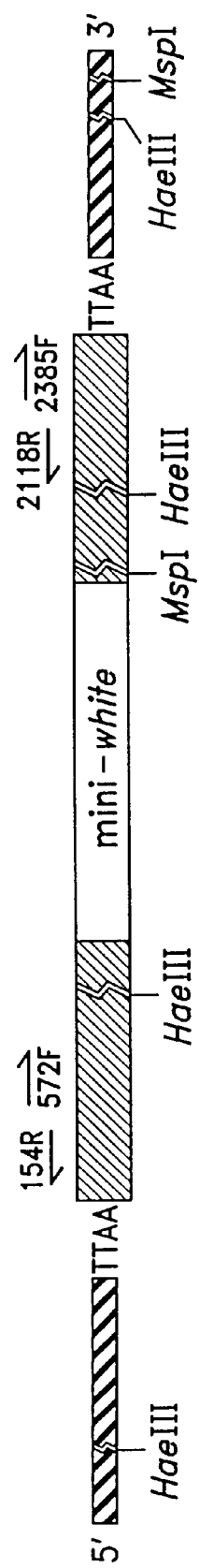
FIGS. 4(a) and (b) show inverse PCR strategy to isolate the pB[Dmw] vector insertion site in transformant sublines.

5'-CCTCGATATACAGACCGATAAAAACACATG-3' (SEQ ID NO 5) were used. PCR products were separated in low-melting-temperature agarose, and fragments were selected that were longer than the respective restriction site terminus distances and different from those expected from the p3E1.2 based vector and helper plasmids. These products were directly subcloned into ddT vectors (Invitrogen), that were sequenced by using primers to vector sequence proximal to the respective termini. Subcloned PCR products were sequenced and analyzed by alignment using Gene-Works 2.5 software (Oxford Molecular Group) and subjected to BLAST analysis (Altshul et al., J. Mol. Biol., Volume 215, 403–410, 1990; herein incorporated by reference) to identify genomic insertion site sequences and distinguish them from those in the injected plasmids. For all the integrations both the 5' and 3' junctions yielded the piggyBac inverted terminal repeat sequences immediately adjacent to a TTAA sequence (SEQ ID NO 1) and proximal insertion site DNA (FIG. 4). The TTAA (SEQ ID NO 1) duplicated target site is characteristic of all piggyBac integrations (Elick et al., Genetica, Volume 97, 127–139, 1995) and typically indicates a vector-mediated transposition. The BLAST analysis revealed that the M17-4 integration occurred in a TTAA site within the cubitus interruptus-Dominant gene located on chromosome 4 at nucleotide 12,898 (GenBank submission U66884; Ahmed & Podemski, Gene, Volume 197, 367–373, 1997), and the M3106 integration was found to have occurred in a TTAA site within a previously sequenced region of the distal X chromosome (GenBank submission AL09193; Murphy et al, direct submission). Determination of insertions in these previously sequenced sites gives the first direct proof that a piggyBac vector does indeed insert into and duplicates TTAA (SEQ ID NO 1) insertion sites in a eukaryotic genome.

Two of the three insertion sites that were sequenced were found to be in previously sequenced genomic loci, and as expected, the insertions sites were all TTAA (SEQ ID NO 1) with one of them within the $ci^D$ allele on the fourth chromosome. Many transposons have insertion site preferences, and for at least some, a clear negative bias against specific sites or loci. This has been clearly demonstrated by genomic hotspots and coldspots for P integration in *D. melanogaster* (See Engels, In: Mobile DNA, D. E. Berg and M. M. Howe, eds., American Society of Microbiology, Washington, D.C., 439–484, 1989), and by differences in preferential integration sites between hobo and P (Smith et al., Genetics, Volume 135, 1063–1076, 1993). If the TTAA (SEQ ID NO 1) specificity for piggyBac integration is not further influenced by proximal sequences, then piggyBac transpositions may find use in transposon-mutagenesis and enhancer traps for loci refractory to P or hobo transpositions in Drosophila.

EXAMPLE V

Figure 10:
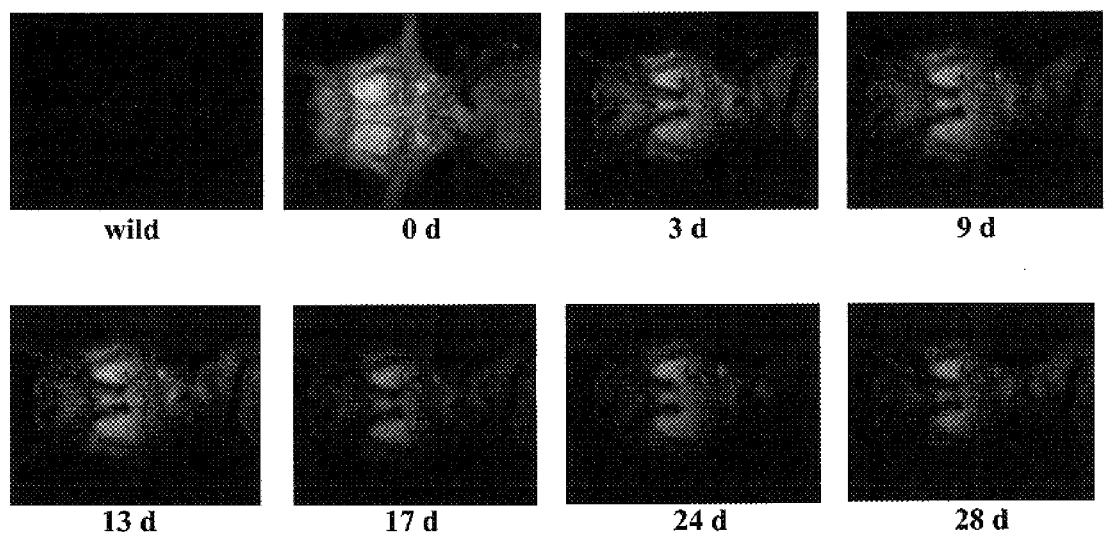
FIG. 10 shows a transgenic insect having three integrations observed under ultraviolet light after various times after decaptitation. Flies were decapitated at day 0, taped in a plastic box placed outdoors in partial sunlight. Digital photographs were taken each day at the same exposure and magnification.

The Caribbean fruit fly, Anastrepha suspensa, was transformed with a piggyBac vector marked solely with PUb-nls-GFP(pB[PUb-nsl-EGFP]) (FIGS. 5 and 6) using the hsp70-piggyBac (phsp-pBac) helper. From injected embryos, 561 surviving G0 adults were intermated in 60 small groups. Four of the G0 groups yielded a total of 57 G1 offspring exhibiting green fluorescence at all stages of developement (See FIG. 7) and chromosomal vector integrations were verified by Southern hybridization for each G0 group. To test GFP as a genetic marker for field released transgenic flies, the perdurance of GFP expression was assayed in transgenic flies killed by decapitation. Two to three day old *A. suspensa* adults transformed with pB[PUb-nls-EGFP], and wild type non-transformed adults, were decapitated and placed within a plastic box kept outdoors in partial shade. GFP fluorescence was observed daily by digital images taken with a SPOT-1 cooled CCD digital camera (Diagnostic Instruments, Inc.) through a Leica MZ-12 stereozoom microscope. All images were taken at the same magnification and exposure parameters. FIG. 10 shows that while GFP fluorescence decreases with time after death, unambiguous detection of GFP is still possible at 28 days after decapitation, with no fluorescence detectable in wild flies. This indicates that the PUb-nls-EGFP marker should be a reliable visible detection system for released transgenic insects, and especially for those captured and killed in field traps with monitoring occurring after extended time periods.

EXAMPLE VI

A piggyBac vector marked with the Mediterranean fruit fly (*Ceratitis capitata*) white gene cDNA (pB[Ccw]) and the phsp-pBac helper was used to transform the oriental fruit fly (*Bactrocera dorsalis*). Injected G0 embryos from the *B. dorsalis* white eye mutant strain yielded 102 fertile adults, that upon individual backcrossing, yielded three lines of putative transformants with pigmented eyes (FIGS. 8a–8e). One of these lines produced 119 G1 transformants. Southern DNA hybridization analysis with piggyBac and white gene probe verified chromosomal integration of the piggyBac-white vector in all three lines. In a separate experiment, the white/PUb-nls-EGFP marker within pB[Ccw, PUb-nls-EGFP] was introduced into a single *B. dorsalis* transformant line from 17 G0 matings. As in Drosophila, the transformant was selected solely by GFP expression, having undetectable eye coloration. This reaffirms the notion that the polyubiquitin-EGFP marker is significantly more reliable than white gene markers.

EXAMPLE VII

Figure 9A:
FIGS. 9(a) and 9(b) show medfly, Ceratitus capitata transformed with piggyBac/white/EGFP vector (pB[Ccw, pUB-nls-EGFP]) expressing eye color under brightfield (9a) and GFP expression under ultraviolet (9b).
Figure 9B:

The PUb-nls-EGFP marker was introduced into the medfly, *Ceratitis capitata*, to further test GFP as a transgenic selection, and to create GFP-marked strains for testing as a field release marker in medfly SIT. First a piggyBac vector marked with PUb-nls-GFP and the medfly white gene (pB [Ccw, PUb-nls-EGFP]) was tested, and then the vector solely marked with Pub-nls-GFP pB[PUb-nls-EGFP]) was tested. Both experiments used the hsp70-piggyBac (phsp-pBAC) helper. Based on GFP fluorescence, the first experiment yielded five transformant lines from 99 fertile G0s (See FIG. 9), while the second experiment yielded three transformed lines from 17 fertile G0 s. Transformation was verified by Southern hybridization analysis.

The foregoing detailed description is for the purpose of illustration. Such detail is solely for that purpose and those skilled in the art can make variations without departing from the spirit and scope of the invention.

I claim:

1. A vector having the nucleotide sequence of SEQ ID NO. 6.

\* \* \* \* \*

SEQUENCE LISTING

<160> NUMBER OF SEQ ID NOS: 14

<210> SEQ ID NO 1
<211> LENGTH: 4
<212> TYPE: DNA
<213> ORGANISM: Trichoplusia ni

<400> SEQUENCE: 1 ttaa                                                                        4

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 2
tcttgacctt gccacagagg                                                      20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 3
tgacacttac cgcattgaca                                                      20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 4
gtcagtccag aaacaacttt ggc                                                  23

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 5
cctcgatata cagaccgata aaaacacatg                                           30

<210> SEQ ID NO 6
<211> LENGTH: 9423
<212> TYPE: DNA
<213> ORGANISM: Artificial Sequence
<220> FEATURE:
<223> OTHER INFORMATION: Description of Artificial
      Sequence:pB[PUb-nls-EGFP]#257

<400> SEQUENCE: 6
gacgaaaggg cctcgtgata cgcctatttt tataggttaa tgtcatgata ataatggttt          60
cttagacgtc aggtggcact tttcggggaa atgtgcgcgg aacccctatt tgtttatttt        120
tctaaataca ttcaaatatg tatccgctca tgagacaata accctgataa atgcttcaat        180

```
aatattgaaa aaggaagagt atgagtattc aacatttccg tgtcgccctt attcccttt    240 ttgcggcatt ttgccttcct gttttgctc acccagaaac gctggtgaaa gtaaaagatg    300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc attttaatt taaaggatc taggtgaaga   1140 tccttttttga taatctcatg accaaaatcc cttaacgtga gttttcgttc cactgagcgt  1200
cagaccccgt agaaaagatc aaaggatctt cttgagatcc ttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca atactgtcc   1380 ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800 ggggggcggag cctatggaaa aacgccagca acgcggcctt tttacggttc ctggcctttt   1860
gctggccttt tgctcacatg ttctttcctg cgttatcccc tgattctgtg ataaccgta   1920 ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgaattcgag ctcggtaccc ggggatcctc tagagtcgac ctgcaggcat   2280
gcaagcttgc atgcctgcag gtcgacgctc gcgcgacttg gtttgccatt cttttagcgcg  2340 cgtcgcgtca cacagcttgg ccacaatgtg ttttttgtca aacgaagatt ctatgacgtg   2400
tttaaagttt aggtcgagta aagcgcaaat ctttttaac cctagaaaga tagtctgcgt   2460
aaaattgacg catgcattct tgaaatattg ctctctcttt ctaaatagcg cgaatccgtc   2520
gctgtgcatt taggacatct cagtcgccgc ttggagctcc cgtgaggcgt gcttgtcaat   2580
```

-continued

```
gcggtaagtg tcactgattt tgaactataa cgaccgcgtg agtcaaaatg acgcatgatt    2640
atcttttacg tgacttttaa gatttaactc atacgataat tatattgtta tttcatgttc    2700
tacttacgtg ataacttatt atatatatat tttcttgtta tagatatcgt gactaatata    2760
taataaaatg ggtagttctt tagacgatga gcatatcctc tctgctcttc tgcaaagcga    2820
tgacgagctt gttggtgagg attctgacag tgaaatatca gatcacgtaa gtgaagatga    2880
cgtccagagc gatacagaag aagcgtttat agatgaggta catgaagtgc agccaacgtc    2940
aagcggtagt gaaatattag acgaacaaaa tgttattgaa caaccaggtt cttcattggc    3000
ttctaacaga atcttgacct tgccacagag gactattaga ggtaagaata acattgttg    3060 gtcaacttca aagtccacga ggcgtagccg agtctctgca ctgaacattg tcagatctcg    3120
agctcaagct tcgaattctg cagtcgacgg tacccgatct tgtcgccgga acgcagcgac    3180
agagattcca atgtgtccgt atctttcagg cttttgccct tcagttccag acgaagcgac    3240
tggcgattcg cgtgtggggt ctgcttcagg gtcttgtgaa ttagggcgcg cagatcgccg    3300
atgggcgtgg cgccggaggg caccttcacc ttgccgtacg gcttgctgtt cttcgcgttc    3360
aaaatctcca gctccatttt gctttcggtg cgcttgcaat cagtactgtc caaaatcgaa    3420
aatcgccgaa ccgtagtgtg accgtgcggg gctctgcgaa aataaacttt tttaggtata    3480
tggccacaca cggggaaagc acagtggatt atatgtttta atattataat atgcaggttt    3540
tcattactta tccagatgta agcccactta aagcgattta acaattattt gccgaaagag    3600
taaaaacaaa tttcacttaa aaatggatta agaaaagctt gtgtaagatt atgcgcagcg    3660
ttgccagata gctccattta aaacacttca aaacaataa gttttgaaaa tatatacata    3720
aatagcagtc gttgccgcaa cgctcaacac atcacacttt taaaacaccc tttacctaca    3780
cagaattact ttttaaattt ccagtcaagc tgcgagtttc aaaattatag ccggtagaga    3840
agacagtgct atttcaaaag caaactaaat aaacaccaat cctaacaagc cttggacttt    3900
tgtaagttta gatcaaaggt ggcattgcat tcaatgtcat ggtaagaagt aggtcgtcta    3960
ggtagaaatc ctcattcagc cggtcaagtc agtacgagaa aggtctcaat ttgaaattgt    4020
cttaaaaata ttttattgtt ttgtactgtg gtgagtttaa acgaaaaaca caaaaaaaaa    4080
gtgatacaca gaaatcataa aaatttttaa tacaaggtat tcgtacgtat caaaaacatt    4140
tcggcacaat ttttttttctc tgtactaaag tgttacgaac actacggtat tttttagtga    4200
ttttcaacgg acaccgaagg tatataaaca gcgttcgcga acggtcgcct tcaaaaccaa    4260
ttgacatttg cagcagcaag tacaagcaga agtaaagcg caatcagcga aaaatttata    4320
cttaattgtt ggtgattaaa gtacaattaa agaacattc tcgaaagtca caagaaacgt    4380 aagttttaa ctcgctgtta ccaattagta ataagagcaa caagacgttg agtaatttca    4440
agaaaaactg catttcaagg tctttgttcg gccatttttt ttttattcaa cgctctacgt    4500
aattacaaaa taagaaattg gcagccacgc atcttgtttt cccaatcaat tggcatcaaa    4560
acgcaaacaa atctataaat aaaacttgcg tgttgatttt cgccaagatt tattggcaaa    4620
ttgtgaaatt cgcagtgacg catttgaaaa ttcgagaaat cacgaacgca ctcgagcatt    4680
tgtgtgcatg ttattagtta gttagttctt tgcttaattg aagtatttta ccaacgaaat    4740
ccacttattt ttagctgaaa tagagtaggt tgcttgaaac gaaagccacg tctggaaaat    4800
ttcttattgc ttagtagttg tgacgtcacc atatacacac aaaataatgt gtatgcatgc    4860
gtttcagctg tgtatatata catgcacaca ctcgcattat gaaaacgatg acgagcaacg    4920
```

```
gaacaggttt ctcaactacc tttgttcctg tttcttcgct ttcctttgtt ccaatattcg    4980
tagagggtta atagggtttt ctcaacaaag ttggcgtcga taaataagtt tcccattttt    5040
attccccagc caggaagtta gtttcaatag ttttgtaatt tcaacgaaac tcatttgatt    5100
tcgtactaat tttccacatc tctattttga cccgcagaat aatccaaaat gcagatcggg    5160
gatcccaccc cacccaagaa gaagcgcaag gtggaggacg atcccgtcgt tttacaacgt    5220
cgtgactggg aaaaccctgg cgttacccaa cttaatcgcc ttgcagcaca tccccctttc    5280
gccagctggc gtaatagcga agaggcccgc accgatcgcc cttcccaaca gttgcggtcg    5340
actctagagg atccccggga tccaccggtc gccaccatgg tgagcaaggg cgaggagctg    5400
ttcaccgggg tggtgcccat cctggtcgag ctggacggcg acgtaaacgg ccacaagttc    5460
agcgtgtccg gcgagggcga gggcgatgcc acctacggca agctgaccct gaagttcatc    5520
tgcaccaccg gcaagctgcc cgtgccctgg cccaccctcg tgaccaccct gacctacggc    5580
gtgcagtgct tcagccgcta ccccgaccac atgaagcagc acgacttctt caagtccgcc    5640
atgcccgaag gctacgtcca ggagcgcacc atcttcttca aggacgacgg caactacaag    5700
acccgcgccg aggtgaagtt cgagggcgac accctggtga accgcatcga gctgaagggc    5760
atcgacttca aggaggacgg caacatcctg ggcacaagc tggagtacaa ctacaacagc    5820
cacaacgtct atatcatggc cgacaagcag aagaacggca tcaaggtgaa cttcaagatc    5880
cgccacaaca tcgaggacgg cagcgtgcag ctcgccgacc actaccagca gaacaccccc    5940
atcggcgacg gccccgtgct gctgcccgac aaccactacc tgagcaccca gtccgccctg    6000
agcaaagacc ccaacgagaa gcgcgatcac atggtcctgc tggagttcgt gaccgccgcc    6060
gggatcactc tcggcatgga cgagctgtac aagtaaagcg gccgcgactc tagatcataa    6120
tcagccatac cacatttgta gaggttttac ttgctttaaa aaacctccca cacctccccc    6180
tgaacctgaa acataaaatg aatgcaattg ttgttgttaa cttgtttatt gcagcttata    6240
atggttacaa ataaagcaat agcatcacaa atttcacaaa taaagcattt ttttcactgc    6300
attctagttg tggtttgtcc aaactcatca atgtatctta aggcgtaaat tgtaagcgtt    6360
aatattttgt taaaattcgc gttaaatttt tgttaaatca gctcattttt taaccaatag    6420
gccgaaatcg gcaaaatccc ttataaatca aagaataga ccgagatagg gttgagtgtt    6480
gttccagttt ggaacaagag tccactatta agaacgtgg actccaacgt caagggcga    6540 aaaaccgtct atcagggcga tggcccacta cgtgaaccat cccctaatc aagtttttg    6600 gggtcgaggt gccgtaaagc actaaatcgg aaccctaaag ggagccccg atttagagct    6660 tgacggggaa agccggcgaa cgtggcgaga aggaaggga agaaagcgaa aggagcgggc    6720
gctagggcgc tggcaagtgt agcggtcacg ctgcgcgtaa ccaccacacc cgccgcgctt    6780
aatgcgccgc tacagggcgc gtcaggtggc acttttcggg gaaatgtgcg cggaacccct    6840
atttgtttat ttttctaaat acattcaaat atgtatccgc tcatgagaca ataaccctga    6900
taaatgcttc aataatattg aaaaaggaag agtcctgagg cggaaagaac cagctgtgga    6960
atgtgtgtca gttagggtgt ggaaagtccc caggctcccc agcaggcaga agtatgcaaa    7020
gcatgcatct caattagtca gcaaccaggt gtggaaagtc cccaggctcc ccagcaggca    7080
gaagtatgca aagcatgcat ctcaattagt cagcaaccat agtcccgccc ctaactccgc    7140
ccatcccgcc cctaactccg cccagttccg cccattctcc gccccatggc tgactaattt    7200
tttttattta tgcagaggcc gaggccgcct cggcctctga gctattccag aagtagtgag    7260
gaggcttttt tggaggaacc attgtgggaa ccgtgcgatc aaacaaacgc gagataccgg    7320
```

-continued

```
aagtactgaa aaacagtcgc tccaggccag tgggaacatc gatgttttgt tttgacggac      7380
cccttactct cgtctcatat aaaccgaagc cagctaagat ggtatactta ttatcatctt      7440
gtgatgagga tgcttctatc aacgaaagta ccggtaaacc gcaaatggtt atgtattata      7500
atcaaactaa aggcggagtg gacacgctag accaaatgtg ttctgtgatg acctgcagta      7560
ggaagacgaa taggtggcct atggcattat tgtacggaat gataaacatt gcctgcataa      7620
attcttttat tatatacagc cataatgtca gtagcaaggg agaaaaggtc caaagtcgca      7680
aaaaatttat gagaaacctt tacatgagcc tgacgtcatc gtttatgcgt aagcgtttag      7740
aagctcctac tttgaagaga tatttgcgcg ataatatctc taatattttg ccaaatgaag      7800
tgcctggtac atcagatgac agtactgaag agccagtaat gaaaaaacgt acttactgta      7860
cttactgccc ctctaaaata aggcgaaagg caaatgcatc gtgcaaaaaa tgcaaaaaag      7920
ttatttgtcg agagcataat attgatatgt gccaaagttg tttctgactg actaataagt      7980
ataatttgtt tctattatgt ataagttaag ctaattactt attttataat acaacatgac      8040
tgttttaaa gtacaaaata agtttatttt tgtaaaagag agaatgttta aaagttttgt       8100
tactttatag aagaaatttt gagttttgt tttttttaa taaataaata aacataaata        8160
aattgtttgt tgaatttatt attagtatgt aagtgtaaat ataataaaac ttaatatcta     8220
ttcaaattaa taaataaacc tcgatataca gaccgataaa acacatgcgt caattttacg      8280
catgattatc tttaacgtac gtcacaatat gattatcttt ctagggttaa ataatagttt      8340
ctaattttt tattattcag cctgctgtcg tgaataccgt atatctcaac gctgtctgtg       8400
agattgtcgt attctagcct ttttagtttt tcgctcatcg acttgatatt gtccgacaca      8460
ttttcgtcga tttgcgtttt gatcaaagac ttgagcagag acacgttaat caactgttca      8520
aattgatcca tattaacgat atcaacccga tgcgtatatg gtgcgtaaaa tatatttttt     8580
aaccctctta tactttgcac tctgcgttaa tacgcgttcg tgtacagacg taatcatgtt      8640
ttctttttg gataaaactc ctactgagtt tgacctcata ttagaccctc acaagttgca       8700
aaacgtggca tttttttacca atgaagaatt taaagttatt ttaaaaaatt tcatcacaga     8760
tttaaagaag aaccaaaaat taaattattt caacagttta atcgaccagt taatcaacgt     8820
gtacacagac gcgtcggcaa aaaacacgca gcccgacgtg ttggctaaaa ttattaaatc      8880
aacttgtgtt atagtcacgg atttgccgtc caacgtgttc ctcaaaaagt tgaagaccaa      8940
caagtttacg gacactatta attatttgat tttgccccac ttcattttgt gggatcacaa      9000
ttttgttata ttttaaacaa agcttggcac tggccgtcgt tttacaacgt cgtgactggg      9060
aaaaccctgg cgttacccaa cttaatcgcc ttgcagcaca tccccctttc gccagctggc      9120
gtaatagcga agaggcccgc accgatcgcc cttcccaaca gttgcgcagc ctgaatggcg      9180
aatggcgcct gatgcggtat tttctcctta cgcatctgtg cggtatttca caccgcatat      9240
ggtgcactct cagtacaatc tgctctgatg ccgcatagtt aagccagccc cgacacccgc      9300
caacacccgc tgacgcgccc tgacgggctt gtctgctccc ggcatccgct tacagacaag      9360
ctgtgaccgt ctccgggagc tgcatgtgtc agaggttttc accgtcatca ccgaaacgcg      9420
cga                                                                    9423
```

<210> SEQ ID NO 7
<211> LENGTH: 19
<212> TYPE: DNA
<213> ORGANISM: Artificial Sequence
<220> FEATURE:

-continued

<223> OTHER INFORMATION: Description of Artificial Sequence:p3E1.2

<400> SEQUENCE: 7
aagcgcaaat cttttttaa         19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:p3E1.2

<400> SEQUENCE: 8
ttaaataata gtttctaat         19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:F1-2

<400> SEQUENCE: 9
aaaaagactg actatttaa         19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:F1-2

<400> SEQUENCE: 10
ttaataagca cactgagtc         19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:M17-4

<400> SEQUENCE: 11
aaaatgtcgt ctaggttaa         19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:M17-4

<400> SEQUENCE: 12
ttaaagccgt atatcagat         19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:M31-6

<400> SEQUENCE: 13
aaatgaacga cttttttaa         19

-continued

```
<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:M31-6

<400> SEQUENCE: 14
ttaatggttt tttagttgt                                              19
```